United States Patent [19]
Perkins et al.

[11] Patent Number: 5,549,139
[45] Date of Patent: Aug. 27, 1996

[54] PNEUMATIC CONTROLS FOR OPHTHALMIC SURGICAL SYSTEM

[75] Inventors: James T. Perkins, St. Charles; Peter F. Appelbaum, St. Louis; John A. Painter, St. Charles, all of Mo.

[73] Assignee: Storz Instrument Company, St, Louis, Mo.

[21] Appl. No.: 449,408

[22] Filed: May 23, 1995

Related U.S. Application Data

[62] Division of Ser. No. 127,921, Sep. 27, 1993, Pat. No. 5,417,246, which is a division of Ser. No. 428,239, Oct. 30, 1989, abandoned.

[51] Int. Cl.⁶ .................................................. F16K 11/10
[52] U.S. Cl. ................................................. 137/884; 137/560
[58] Field of Search ........................................ 137/883, 884, 137/560

[56] References Cited

U.S. PATENT DOCUMENTS

| | | | |
|---|---|---|---|
| Re. 33,229 | 6/1990 | Schwaber | 364/709.01 |
| 3,360,185 | 12/1967 | Wooldridge | 230/12 |
| 3,599,639 | 8/1971 | Spotz | 128/276 |
| 3,693,613 | 9/1972 | Kelman | 128/24 A |
| 3,812,855 | 5/1974 | Banko | 128/276 |
| 3,920,014 | 11/1975 | Banko | 128/230 |
| 4,019,514 | 4/1977 | Banko | 128/230 |
| 4,024,185 | 5/1977 | Lee | 260/563 R |
| 4,024,866 | 5/1977 | Wallach | 128/276 |
| 4,084,250 | 4/1978 | Albertine et al. | 364/708 |
| 4,168,707 | 9/1979 | Douvas et al. | 128/276 |
| 4,180,074 | 12/1979 | Murry et al. | 128/276 |
| 4,324,243 | 4/1982 | Helfgott et al. | 128/276 |

(List continued on next page.)

FOREIGN PATENT DOCUMENTS

| | | |
|---|---|---|
| 0121277 | 10/1984 | European Pat. Off. . |
| 0232458 | 8/1987 | European Pat. Off. . |
| 0362822 | 4/1990 | European Pat. Off. . |
| 0074642 | 6/1980 | Japan . |
| 0146336 | 8/1984 | Japan . |
| 0176834 | 10/1984 | Japan . |
| 2147126 | 5/1985 | United Kingdom . |

OTHER PUBLICATIONS

Catalog, 37 Minimatic Electronic/Pneumatic Interface Valves, Clippard Minimatic®, Catalog 984–R2, ©1985, Clippard Instrument Laboratory, Inc.
Brochure, Clippard Minimatic®, p. 7.
Brochure, "Series NZ3o25, NZ3o45, SMC, Solenoid Controlled Pilot Operated Valves", SMC Pneumatics Inc., NZ30M–1, Aug. 1985.
Brochure, "Series NVJ100", SMC Pneumatics Inc.

*Primary Examiner*—John C. Fox
*Attorney, Agent, or Firm*—David A. Warmbold; Montgomery W. Smith

[57] ABSTRACT

A pneumatic control system for providing pressurized air and vacuum to ophthalmic microsurgical instruments. The pneumatic system is constructed in a drawer assembly to allow it to be readily inserted into or removed from a modularly construct ed cabinet of a microsurgical control console.

In addition, the pneumatic system improves upon existing pneumatic control systems by providing a third mode of microscissors operation from a single pneumatic port. The third mode is made possible by a high speed three-way solenoid control valve which provides rapid pulses of air to the pneumatic port.

A second improvement involves the use of a pneumatic pressure transducer to monitor pneumatic pressure being supplied to the pneumatic system in order to recognize non-hazardous transient drops in air pressure which can occur under certain normal operating conditions, A third improvement relates to the use of an intraocular pressure accumulator downstream from a final solenoid-operated pinch valve, which reduces fluctuations in air pressure and has other advantages.

4 Claims, 9 Drawing Sheets

U.S. PATENT DOCUMENTS

| | | | |
|---|---|---|---|
| 4,395,258 | 7/1983 | Wang et al. | 604/65 |
| 4,441,357 | 4/1984 | Kahn et al. | 73/40 |
| 4,468,219 | 8/1984 | George et al. | 604/66 |
| 4,479,494 | 10/1984 | McEwen | 128/327 |
| 4,479,761 | 10/1984 | Bilstad et al. | 417/395 |
| 4,493,698 | 1/1985 | Wang et al. | 604/51 |
| 4,559,705 | 12/1985 | Hodge et al. | 33/1 B |
| 4,567,481 | 1/1986 | Meier et al. | 340/784 |
| 4,622,503 | 11/1986 | Sundblom et al. | 318/645 |
| 4,650,460 | 3/1987 | Roizenblatt | 604/22 |
| 4,664,601 | 5/1987 | Uchida et al. | 417/27 |
| 4,665,466 | 5/1987 | Green | 361/384 |
| 4,670,006 | 6/1987 | Sinnett et al. | 604/26 |
| 4,706,687 | 11/1987 | Rogers | 128/752 |
| 4,727,791 | 3/1988 | Satoh | 91/47 |
| 4,740,202 | 4/1988 | Stacey et al. | 604/119 |
| 4,757,814 | 7/1988 | Wang et al. | 128/318 |
| 4,758,925 | 7/1988 | Obata et al. | 361/384 |
| 4,759,349 | 7/1988 | Betz et al. | 128/6 |
| 4,770,187 | 9/1988 | Lash et al. | 128/760 |
| 4,770,654 | 9/1988 | Rogers et al. | 604/22 |
| 4,790,816 | 12/1988 | Sundblom et al. | 604/31 |
| 4,803,471 | 2/1989 | Rowland | 340/626 |
| 4,810,242 | 3/1989 | Sundblom et al. | 604/28 |
| 4,825,802 | 5/1989 | Le Bec | 116/70 |
| 4,837,857 | 6/1989 | Scheller et al. | 455/617 |
| 4,838,281 | 6/1989 | Rogers et al. | 128/752 |
| 4,850,377 | 7/1989 | Parker et al. | 128/898 |
| 4,870,964 | 10/1989 | Bailey, Jr. et al. | 128/303.1 |
| 4,898,579 | 2/1990 | Groshong et al. | 604/67 |
| 4,899,254 | 2/1990 | Fercham et al. | 361/384 |
| 4,902,276 | 2/1990 | Zakko | 604/28 |
| 4,933,843 | 6/1990 | Scheller et al. | 364/413.01 |
| 4,957,107 | 9/1990 | Sipin | 128/204.21 |
| 4,988,336 | 1/1991 | Kohn | 604/67 |
| 5,000,226 | 3/1991 | Stoll et al. | 137/884 |
| 5,020,535 | 6/1991 | Parker et al. | 606/174 |
| 5,065,794 | 11/1991 | Cheung | 137/883 |
| 5,071,411 | 12/1991 | Hillsteac | 604/246 |
| 5,091,656 | 2/1992 | Gahn | 307/119 |
| 5,107,899 | 4/1992 | Murphy | 137/884 |
| 5,301,717 | 4/1994 | Goedeche | 137/884 |

PNEUMATIC CONTROLS FOR OPHTHALMIC SURGICAL SYSTEM

This is a divisional of application Ser. No. 08/127,921 filed on Sep. 27, 1993, now U.S. Pat. No. 5,417,246, which is a divisional of U.S. Ser. No. 07/428,239, filed Oct. 30, 1989, now abandoned.

BACKGROUND OF THE INVENTION

1. Cross-Reference to Related Applications

The present invention is related to the subject matter of the following commonly assigned co-pending application Ser. No. 07/267,713 filed Nov. 4, 1988, which is a continuation of application Ser. No. 06/928,170 filed Nov. 6, 1986 and entitled "Control System For ophthalmic Surgical Instruments."

The present invention is related to the subject matter of the following commonly assigned applications being filed concurrently on even date herewith:

Application Ser. No. 07/428,232 entitled "Control System For Ophthalmic Surgical Instruments", now abandoned;

Application Ser. No. 07/428,354 entitled "Control System For Calibrating And Driving Ultrasonic Transducer", now abandoned;

Application Ser. No. 07/427,614 entitled "Remote Control Console For Surgical Control System", now U.S. Pat. No. 5,249,121;

Application Ser. No. 07/428,125 entitled "Vitrectomy Probe", now U.S. Pat. No. 5,047,008;

Application Ser. No. 07/428,216 entitled "Modular Cabinet For Surgical Control Systems", now abandoned;

Application Ser. No. 07/428,355 entitled "Footswitch Assembly With Electrically Engaged Detents", now U.S. Pat. No. 5,091,656; and Application Ser. No. 07/428,166 entitled "Motorized IV Pole Assembly", now abandoned.

The disclosures of each and every one of the above-referenced applications is hereby incorporated herein by reference.

2. Field of the Invention

The present invention relates in general to pneumatic control circuits and systems for providing controlled levels of pressurized air or vacuum to instruments used during ophthalmic microsurgical procedures, and in particular to improvements in such pneumatic circuits and to a method of modularly constructing such pneumatic circuits within a drawer assembly.

3. Description of Related Art

In the ophthalmic microsurgical arts, a number of different procedures which require pressurized air or vacuum are known. For example, aspiration, that is providing suction via a controlled vacuum level, is used widely for various procedures and with various instruments. Aspiration is used, for example, during the engagement, stripping and removal of residual lens cortical material in extra-capsular cataract extraction and phacoemulsification procedures. Phaco-fragmentation procedures also make use of aspiration. Anterior and posterior vitrectomies also require aspiration for the removal of cut material from the eye, such as vitreous.

Intraocular pressure (IOP) control provides precisely adjusted delivery of filtered air to the eye during posterior ocular pressure procedures. Also, the IOP system can be used to pressurize an irrigation supply of balanced salt solution for the eye during anterior segment procedures. Microscissors are another ophthalmic microsurgical instrument which are often pneumatically driven. Three different scissor drive modes are known today: single cut mode, variable rate cut mode, and proportional cut mode.

While a variety of pneumatic systems are known for providing the appropriate pressurized air or vacuum signals required for the aforementioned microsurgical procedures or instruments, there nevertheless remains an interest in improving the quality of operation of these devices and making such pneumatic control systems (1) more powerful, in terms of the number of functions supported, (2) more accurate in the sense of precisely providing the desired pneumatic pressure or vacuum signals, and (3) easier and simpler to service and/or repair when necessary.

The assignee of the present invention, namely Storz Instrument Co. of St. Louis, Mo. (hereinafter "Storz"), has marketed an ophthalmic microsurgical system under the trademark "DAISY" which is housed in a single control console and which supports all the pneumatic functions described above, except for (1) pressurizing an irrigation supply for anterior segment procedures, and (2) multi-cut scissors mode. It is one object of the present invention to provide all of the foregoing pneumatic functions, including the two last mentioned, in a manner that satisfies the three aforementioned interests.

The DAISY console, a pressure switch is used to monitor the incoming air pressure of the main supply line that provides air to the pneumatic system. The purpose of pressure switch is to detect abnormally low air pressure conditions which can exist, for example, if the hospital air supply pressure falls beneath expected levels or if some other problem interrupts the air supply to the DAISY console. In the DAISY console, this pressure switch is set to trip out at an appropriate level, such as 80 psig. Through experience with the DAISY pneumatic system, it has been found, that under certain transient conditions, namely low but acceptable pressure levels from the hospital supply line when user requests for high vacuum levels are initiated, demand for the pressurized air momentarily outstrips the ability of the hospital line to supply same on account of very brief delays in pressurized air movement. Such transient conditions on occasion cause the pressure switch to indicate that the air pressure is low, at which time the microsurgical console warns the surgeon of the low air supply condition. However, study has shown that such transient conditions, if of sufficiently short duration, are non-hazardous and the surgeon need not be warned or otherwise interrupted. Thus it is an object of the present invention to provide a pneumatic control system which can handle non-hazardous transient air pressure drops, which still recognizing and correctly responding to transient air pressure drops which do indicate that a warning to the surgeon of the low air pressure condition is required or desirable.

With advances in ophthalmic microsurgical techniques, there is increasing interest and need for a highly accurate IOP system which is capable of delivering controlled low pressure air with a minimum amount of pulsations or other variations in pressure. IOP systems typically operate in the range of 0 to 100 mmHg. At these pressure levels, it has not been possible previously, using on/off solenoid control valves, to ramp up air pressure to a desired setting in this range without overshoot. Further, in prior art IOP systems, there is a discernable variation in the output pressure of the IOP system from the desired pressure setting by as much as plus or minus four mmHg or more. Thus, is an object of the present invention to provide an IOP system which uses inexpensive on/off solenoid control valves, and yet still avoids overshoot and minimizes pressure variations from the desired IOP setting.

SUMMARY OF THE INVENTION

To meet at least one of the foregoing objectives, there is provided in accordance with the first aspect of the present invention, a method of avoiding a nuisance occurrence of a safety procedure due to momentary dips in gas pressure caused by initiation of relatively high volume gas flow in the electropneumatic control system of a microsurgical control console. The control system is the type that has at least one pressure regulation means for limiting gas pressure downstream to a predetermined value, vacuum generation means, including at least one venturi for producing of vacuum from pressurized gas flow, and pressure sensing means for producing an electrical signal in response pressure at a predetermined location downstream from the regulation means and upstream from the vacuum generation means. The method comprises the steps of: (a) making the pressure sensing means a pressure transducer means for producing an analog signal accurately corresponding to actual pressure at the predetermined location; (b) monitoring the pressure at the predetermined location with the pressure transducer means to observe when pressure at the location falls beneath a minimum acceptable level; (c) monitoring the length of time that monitored pressure is continuously beneath the minimum acceptable value; and (d) instituting a safety procedure in the control console when the length of time that the monitored pressure is below the minimum acceptable value exceeds a predetermined length of time.

To meet another one of the foregoing objectives, there is provided, according to a second aspect of the present invention, an improved intraocular pressure (IOP) control system of the type powered by a source of compressed gas. IOP control system includes the following components: at least one pressure regulation means for limiting gas pressure to a predetermined maximum value; first electromagnetically-actuated valve means for controlling flow of the compressed gas from its source to a location where such gas is put to use; and a second electromagnetically-actuated valve means for controlling flow of the compressed gas from the location to atmosphere to reduce pressure at such location. The improvement in this basic control system comprises: a third electromagnetically-actuated valve means for interrupting flow from the first valve means to the location; and variable volume gas reservoir means for accumulating additional compressed gas for later use, the reservoir means being located downstream of the first and third valve means.

To meet yet another one of the foregoing objectives, there is provided, according to a third aspect of the present invention, an improved electropneumatic control system which provides a high-speed multi-cut mode in addition to a single cut mode and a proportional mode. The system is of the type that is powered by a source of compressed gas such as air and includes at least one pressure regulator means for limiting gas pressure to a predetermined maximum value, and a first electromagnetically-actuated valve means for controlling flow of the compressed gas from the source to a location where the gas is put to use operating a microscissors or like gas-actuated microsurgical instrument. The improvement comprises the combination of the foregoing two means and a second electromagnetically-actuated valve means, connected In parallel to and operating independently of the first valve means. The second valve means cyclically controls the flow of compressed gas from the pressure regulator means to the location. The second valve means makes it possible to have a multi-cut mode for operating the microscissors or like instrument. The second valve means is preferably a three-way, normally closed, two-position, solenoid-operated, spring-returned control valve.

These and other aspects, advantages and objects of the methods and pneumatic system of the present invention may be further understood by referring to the detailed description, accompanying figures and dependent claims.

BRIEF DESCRIPTION OF THE DRAWINGS

The drawings form an integral pad of the description of the preferred embodiments and are to be read in conjunction therewith. Like reference numerals designate the same or similar components or features in the various Figures, where:

FIG. 2 is a front view of the FIG. 1 control console showing the lay-out of the CRT visual display, control buttons or keys, surgical instrument connection ports and the like;

DETAILED DESCRIPTION OF THE PREFERRED EMBODIMENTS

Figure 1A:
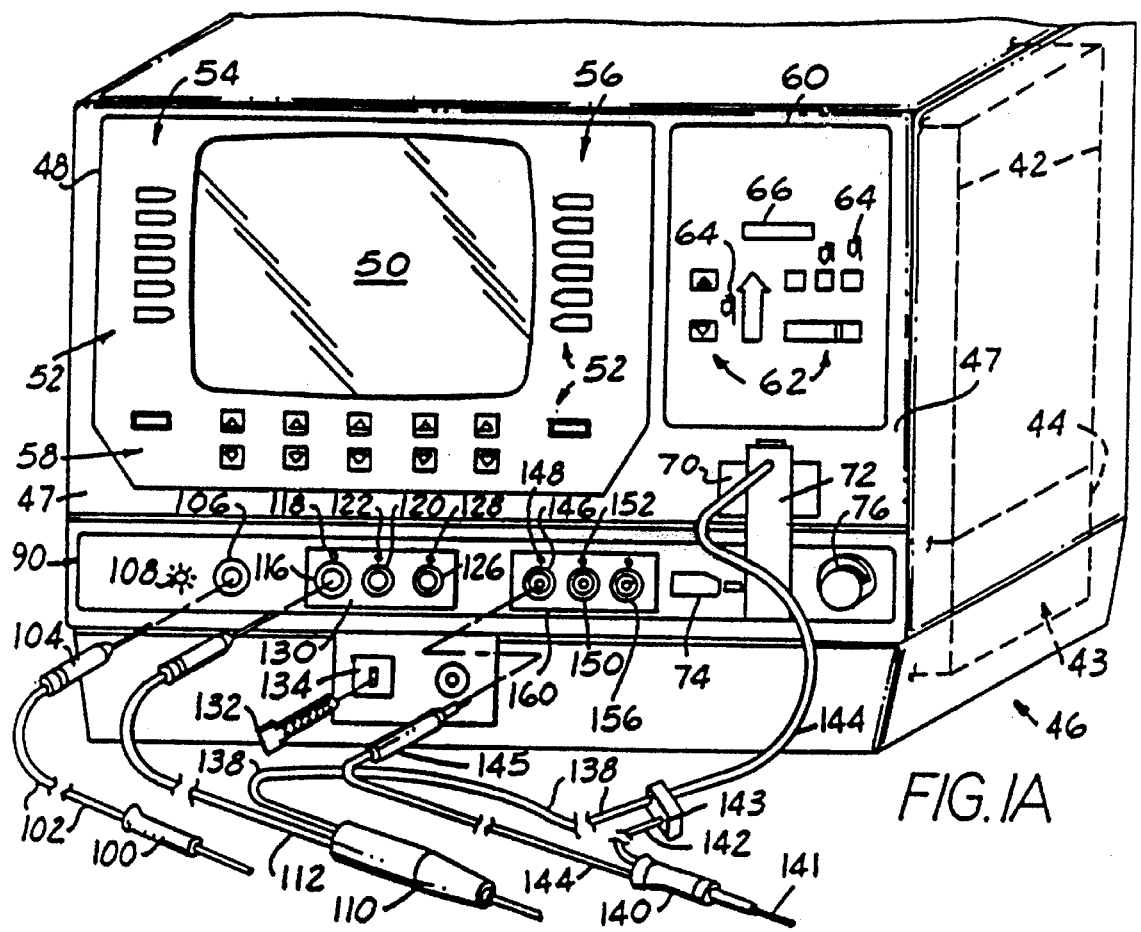
FIGS. 1A and 1B are front and back perspective views of an ophthalmic microsurgical control console which utilizes the pneumatic control system of the present invention.
Figure 1B:
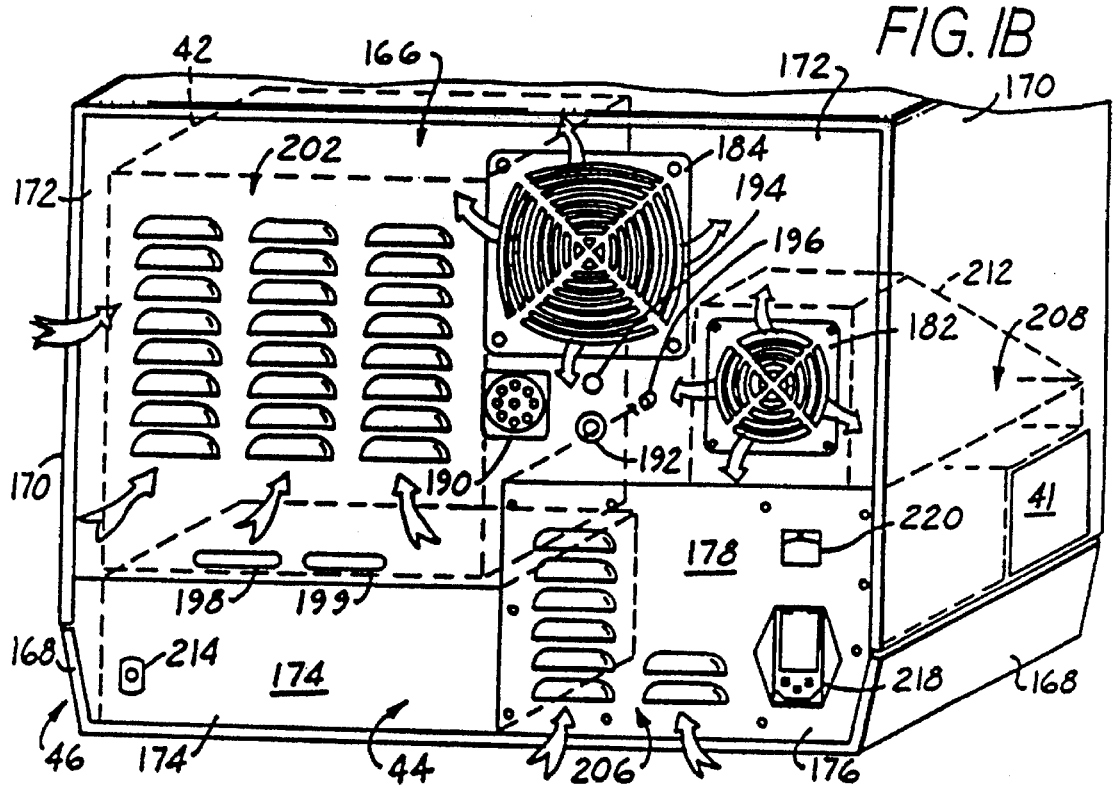
Figure 2:
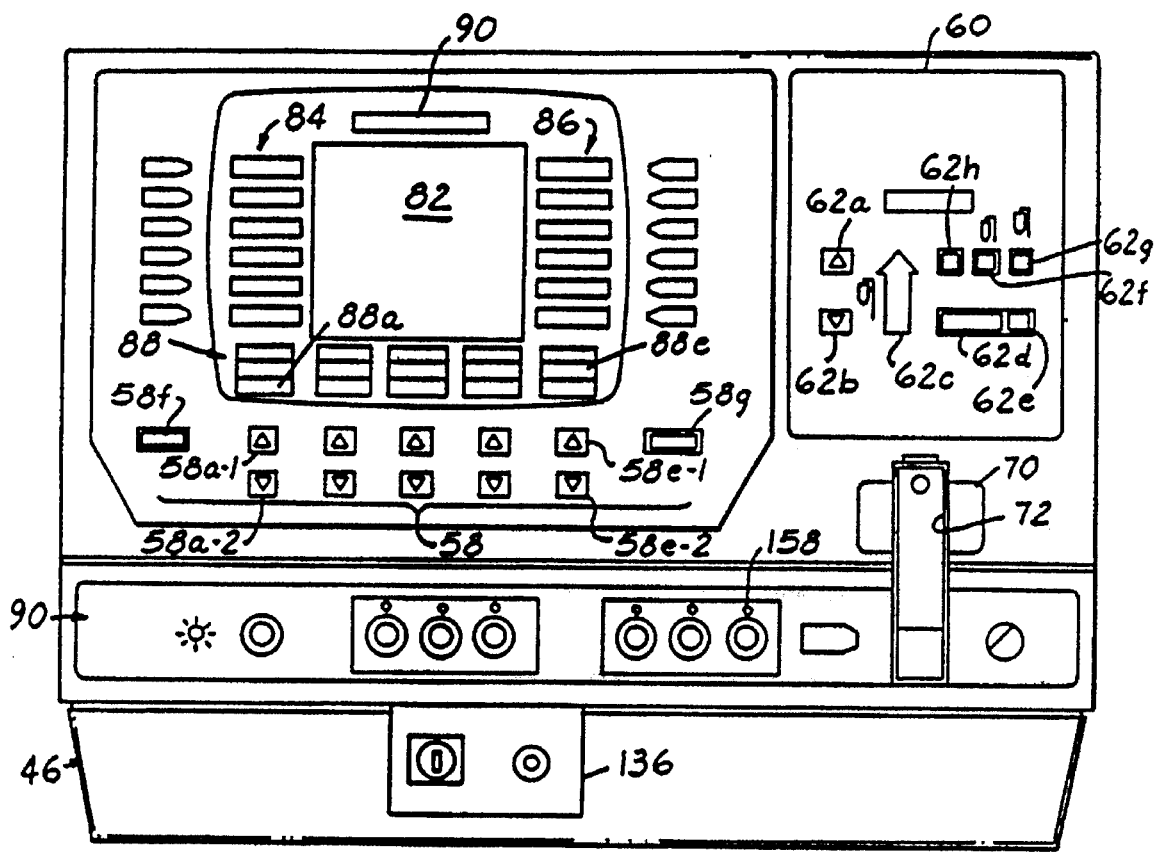

I. General
A. Front of Control Console (FIG. 1A)
 1. Display & Keys of Primary Panel
 FIGS. 1A, 1B and 2 show a microsurgical control system 40 provided with an illumination lamp drawer 41, an electronic control system housed in pad in a nine-board electronic card rack 42, and a pneumatic control system 43 housed primarily in a pneumatic drawer module 44, and other modules which will be described later. The control system 40 includes a system console 46 which has an upwardly and slightly inwardly-sloping front surface 47 with a primary front panel 48. On the front panel 48 is an electronic display screen 50, a plurality of pushbuttons or touch sensitive pads 52 organized in two groups 54 and 56 along the left and right sides of the display screen 50, and a third group 58 along the bottom of the display screen 50. Additionally, there is a secondary front panel 60 located to the right of front panel 48 which has additional pushbuttons or pads 62, indicator lights 64 and information readout 66. The console 46 also includes a slot 70 for a conventional Storz aspirant collection cassette 72, a cassette eject button 74 and an irrigation pinch valve assembly 76.

The electronic display screen 50 is controlled by a microcomputer within the console 46 to provide several different menus or messages which instruct the operator as to the function of the pushbuttons 52 through 62. The operation of the display screen 50 in combination with the buttons 52–62 may be best understood by looking at the enlarged view in FIG. 2. The display screen 50 is shown there as being conceptually divided into central display screen region 82, left-side display region 84, right-side display region 86, bottom display region 88 and a top display region 90. The side regions 84 and 86 each consist of six horizontal fields stacked one above the other and positioned to correspond to the locations of buttons in button groups 54 and 56. By virtue of the adjacent location of the top button of button group 54 and the top field of region 84, for example, a message in the upper left-hand corner of the screen 50, i.e., in this top field, is readily understood by the operator as referring to the upper leftmost button. The other buttons and fields are similarly paired. This arrangement allows the indicated function of each of the buttons 54 or 56 to be readily changed by simply just changing the legend displayed in its adjacent field. In a similar manner, each pair of buttons, such as buttons 58*a*-1 and 58*a*-2, is associated with one of the three-part fields of bottom region 88, such as region 88*a*. In general, the upper row of buttons, i.e., buttons 58*a*-1 through 58*e*-1 are used to increment a setting or parameter displayed in the corresponding region 88*a*–88*e* of screen 50 directly above, while the buttons in the lower row, i.e., buttons 58*a*-2 through 58*e*-2, are used to decrement such displayed settings or parameters. The use of an electronic display screen also permits the legends for buttons 52, 54 and 56 to be labeled in virtually any language. Button 58*f* is used to bring up an information screen on display 50 to assist the operator, such as by further explaining functions associated with choices on the display menu. Button 58*g* is used to return to an earlier menu screen in a chain of related menus or other screens.

2. Surgical Instrument Connector Panel

The microsurgical control system 40 is capable of operating a number of different microsurgical instruments. To provide for this functionality, there is a row of different types of connector receptacles on surgical instrument connector panel 90 which permits various instruments to be plugged in or otherwise controlled by the control system 40 as may be seen in FIGS. 1A and 2, indicator lights are provided adjacent to or above each of the connector receptacles for indicating when the connector is activated or functional.

a. Illumination Instrument

FIG. 1A shows a fiber optic illumination instrument 100 coupled to console 46 via fiber-optic cable 102 which extends out of male illumination connector plug 104 designed for insertion into illumination connector receptacle 106. Indicator lamp 108 is illuminated whenever the fiber optic illumination (FOL) lamp inside console 46 is lit.

b. Electrically Powered Instruments

Phaco fragmentation handpiece 110 is a conventional piezoelectric device for disintegrating hard objects such as intraocular cataractous material utilizing ultrasonic ("US") energy transmitted to its needle 112. Electrical power pulsating at US frequency is provided to handpiece 110 via power cable 112 attached to phaco connector plug 114, which is designed to be inserted into phaco female connector 116. Light 118 indicates when US frequency electrical power is being delivered to 116. Female connector 120 is designed to receive a male connector plug 120 for powering a conventional bipolar coagulator handpiece. Indicator light 122 indicates when this connector 120 is operational. Female connector 126 is used for receiving a male connector plug (not shown) of a conventional CAC handpiece. (CAC stands for "controlled anterior capsulotomy.") Indicator 128 illuminates when the CAC function is activated. Thus it will be seen that the three connectors 116, 120 and 126 grouped together on rectangular plate 130 all relate to electrically powered surgical functions.

c. Fluid-Powered Instruments

Certain microsurgical instruments are actuated or controlled by fluid pressure (either positive pressure or negative pressure, or both). The phaco fragmentation instrument 110, for example, utilizes aspiration through hollow flexible plastic tubing 138 to remove disintegrated materials, which are collected along with aspirant in the cassette 72.

Vitrectomy probe 140 includes a hollow needle 141 having an inner tube which reciprocates to cut intraocular material sucked in a small hole near the tip of the needle. The inner tube (not shown) reciprocates on account of pulsating air pneumatic drive signal delivered to a spring-returned piston (not shown) to which the inner tube is connected. The suction pad of this instrument is also coupled to the collection container 72 by tubing 142. (Bracket 143 is intended to indicate that either tube 142 or tube 138 may be connected to the remaining portion of tube 144 which leads to the collection cassette 72.) Tubing 144 extending from the probe 140 leads to male connector plug 45 which is inserted into vitrectomy connector receptacle 146. Light 148 indicates when the connector is activated. Connector 146 supplies the pulsating air drive signal to the vitrectomy probe from a pneumatic circuit which will later be described. A conventional vitrectomy probe in the form of a guillotine cutter such as the Storz Microvit probe may be used. Alternatively, the improved probe described in aforementioned application Serial No. _____ entitled "Vitrectomy Probe" may be used as probe 140.

Connector receptacle 150 provides access to an intraocular pressure (IOP) system, and indicator light 152 indicates when connector 150 is actuated. Connector 156 is used to deliver a pneumatic drive signal to conventional pneumatically operated microscissors (not shown), which can be operated in any one of three modes as will be further explained. Indicator light 158 is illuminated when any one of the three scissors modes is enabled. In light of the foregoing description, it will be appreciated that the three connectors 146, 150 and 156 located on rectangular plate 160 all relate to surgical functions implemented via the pneumatic system of console 46.

While certain microsurgical instruments have been illustrated or described in connection with FIG. 1A, it should be understood that the microsurgical control system 40 can be used with other instruments of a similar type. In general, any microsurgical instrument that is actuated or controlled by fluid pressure (whether positive or negative), can be made to operate with the pneumatic control system of the present invention.

d. Irrigation Pinch Valve

The irrigation pinch valve assembly 76 is utilized to provide on/off control for the gravity-infused salt solution held in the IV bottle. The pinch valve is operated by an on/off solenoid of the pneumatic system as will be further explained. Display 66, which may be an LED display or the like, indicates the height of the IV pole above the minimum reference height established via the zero switch 62e.

3. Off-line Memory Storage of User Data

On occasion, it is desirable to store selected operating values or set-up parameters for a particular surgeon or microsurgical operation in off-line memory. A removable memory key 132 is provided for this purpose. The key 132 includes an integrated memory circuit which stores such operating values or set-up parameters. Console 46 receives the key 132 through a key receptacle interface 134 mounted in plate 136. Suitable types of memory keys and receptacle interfaces are commercially manufactured by Datakey, Inc. of Burnsville, Minn. However, it should be appreciated that other suitable means for storing particular user data may be employed with the console 46 as well, such as electronic cards with memory, magnetic disk media, or the like.

4. Display & Keys of Secondary Panel (FIG. 2)

The functions associated with the secondary panel 60 will now be described. As best seen in FIG. 2, panel 60 is used to control a motorized IV pole (not shown) that supports one or more bottles or pouches of balanced solution used to provide irrigation during ophthalmic surgical procedures. The motorized IV pole includes a reversible electric motor/gear reducer combination which adjusts the height of the IV pole up or down as desired. The particular height may be selected via the buttons on control panel 60. Buttons 62a and 62b are used to lower and raise the pole incrementally, as long as the button is held. Button 62c is used, under emergency conditions, to send the pole upward rapidly to its maximum height, and indicator emblem 64c is illuminated when this function is activated. Button 62d, when depressed, automatically lowers the IV pole to a convenient height to facilitate changing of the IV bottle. Button 62e is called the "zero switch" because when pressed it establishes the zero reference, i.e., the minimum height for the IV pole. Button 62f and 62g are used respectively to change the height for the IV pole to either a first or second preset level. Button 62h is used during set-up to specify the first and second preset heights of the IV pole. The operation of these functions and the construction of the "Motorized IV Pole Assembly" is described in aforementioned application of the same title.

B. Rear of Control Console (FIG. 1B)

FIG. 1B shows the rear of the system console 46, including the rear surface 166. The console 46 includes a base frame or chassis 168, a sheet metal cover 170 having three sides forming an inverted U-shape, and back cover plate 172 occupying roughly the top two-thirds of the surface 166. The bottom one-third of the rear surface 166 is occupied by the rear wall 174 of pneumatic drawer module 44 shown in phantom, and the rear wall 176 of electrical power drawer 178 which is also partially shown in phantom and will be later described. Mounted on the upper rear cover plate 172 are the following devices: small ventilation fan 182, a large ventilation fan 184, an electrical connector receptacle 190 for a footpedal controller, an IV pole connector receptacle 192, an accessory connector receptacle 194 and a CRT screen brightness control knob 196. Cover slots 198 and 199 are also provided for future expansion to allow addition of RS232 communication ports. Rear cover plate 172 includes a set 202 of 24 ventilation louvers arranged in three columns. Rear wall 176 of power electrical drawer 178 includes a set 206 of eight ventilation louvers arranged as shown. Both sets 202 and 206 of louvers allow air to be drawn inside of the console 46. Air drawn in through louvers 202 circulates internally and eventually exits at exhaust fan 184, while air drawn in through louvers 206 is substantially confined to circulate within the electrical drawer 178 and past the lamp drawer 41 since it is confined by shelf/cover 208 and plenum 212 to be exhausted by ventilation fan 182.

The main pneumatics supply connection to pneumatics drawer 44 is made through a male Schrader quick-disconnect fitting 214 in the lower left rear corner of rear wall 174. Electrical power is provided to the electrical drawer module 178 via electrical receptacle and fuse holder assembly 218. A main on/off electrical power switch 220 for turning the console 46 on or off, is located above receptacle 218. The various hardware assemblies and drawers of console 46 are constructed in a highly modular, easy-to-assemble and easy-to-service manner described in detail in aforementioned application Ser. No. _____ entitled "Modular Cabinet For Surgical Control System."

II. Surgical Modes & User Interface in General

A. Switch-Selectable Surgical Modes & Features

The control console 46 is the head and brain of the multi-function microsurgical system 40. The system 40 supports up to nine switch-selectable modes which are used in either or both anterior segment and posterior segment ophthalmic surgery. These modes are: (1)irrigation only, (2)irrigation/aspiration, (3) phaco (either emulsification or fragmentation), (4) vitrectomy, (5) controlled anterior capsulotomy (CAC), (6) bipolar, (7) scissors, (8) illumination, and (9) intraocular pressure (IOP) control. Each mode is automatically integrated into the system 40 in a manner appropriate to the type of operation selected by the operator via keys 52–58.

1. Irrigation mode employs a footpedal on/off control of irrigation. This operating mode is intended for use during an anterior capsulotomy and other anterior segment procedures in which irrigation without aspiration is desired.

2. Irrigation/aspiration mode provides footpedal on/off control over irrigation and linear footpedal control over aspiration. This mode is intended for use in the engagement, stripping and removing of residual lens conical material in extracapsular cataract extraction and phacoemulsification procedures.

3. Phaco mode implements the phacoemulsification and phacofragmentation functions, which are available for both anterior and posterior segment procedures. Under phacoemulsification procedures, a "fixed phaco" mode is available in which the phaco power and aspiration levels are set via the console controls, and "linear phaco" mode is available in which phaco power is footpedal controlled and aspiration level is determined by the console controls. For phaco fragmentation procedures, a fixed phaco mode controls aspiration via the footpedal.

4. Vitrectomy mode makes the vitrectomy function available for both anterior and posterior segment procedures. For anterior vitrectomy, footpedal on/off control is provided for vitreous cutting and irrigation, while linear footpedal control is provided for aspiration. For posterior vitrectomy, this mode provides footpedal/on-off control over vitreous cutting and linear footpedal control over aspiration.

5. CAC mode provides footswitch on/off control of a CAC probe, and is explained further in connection with the discussion of FIG. 4D below.

6. Bipolar mode provides on/off control of bipolar power via the footpedal assembly, and is described further in the discussion of FIG. 4D below.

7. Scissors mode enables the posterior surgeon to employ a pneumatically driven intraocular scissors in any one of three foot-pedal controlled cutting operations: single cut, variable rate or proportional, which will be explained in more detail later.

8. Illumination mode provides fiber-optic illumination to facilitate viewing the posterior segment during posterior procedures. The light source thereof is adjustable from approximately five-percent illumination to full brilliance. Automatic lamp switching provides back-up illumination if the primary lamp should fail.

9. IOP mode provides precision regulated console-adjusted delivery of filtered air to the eye during posterior ocular pressure procedures. Alternatively this mode can be used to pressurize an irrigation supply to the eye for anterior procedures.

Many of the foregoing modes and features are also found in the Storz DAISY console. For example, like DAISY console, console 46 uses a disposable transparent cassette to collect aspirant during surgery. When the cassette is fully inserted into the cutout slot 70 in the console 46, the system 40 will automatically secure the cassette via a solenoid-actuated valve, and a vacuum connection will be established at that time.

10. Additional Surgical Features. The system 40 also includes additional features, namely, aspiration prime and irrigation prime in the same manner implemented in the DAISY console. Further, the special repeat reflux procedure is supported by the control console 46 in order to allow a handpiece to be cleared with pneumatic pressure if it becomes clogged with tissue. This reflux feature is available in all anterior modes, and consists of repeated reflux action.

B. User Interface Strategy

The integration of all of the aforementioned functions into a single console 46 represents a formidable organizational challenge since the system 40 must provide the operator(s) with a straightforward means of invoking all of the different modes, the functions under each mode, and a way to adjust the various set-up and operating parameters associated with various electronic control circuits and pneumatic control systems. The CRT display and pushbutton arrangement assists system flexibility greatly in this regard since it is possible to reprogram the functions of the switches 52 in accordance with the selected anterior segment or posterior segment procedure or with the selected utility functions, such as establishing set-up values or configuring the system for a particular surgeon's use.

Similarly, the use of a microprocessor-based control system, described in FIG. 4, enables the various strategies for the control functions to be stored in memory and called upon as required. To reduce cost of construction and assembly time, to increase reliability and serviceability, the various components of the surgical system have been constructed as separate modules or subassemblies where possible. This approach is evident in the electronics portion and pneumatics portion of the control system 40. Where practical, distinct electrical functions have been placed on their own printed circuit board which is separately addressed by the microprocessor. Similarly, the pneumatics functions have been collected and placed in one drawer module to allow easy installation and replacement.

III. Footswitch Assembly (FIG. 3)

Figure 3:
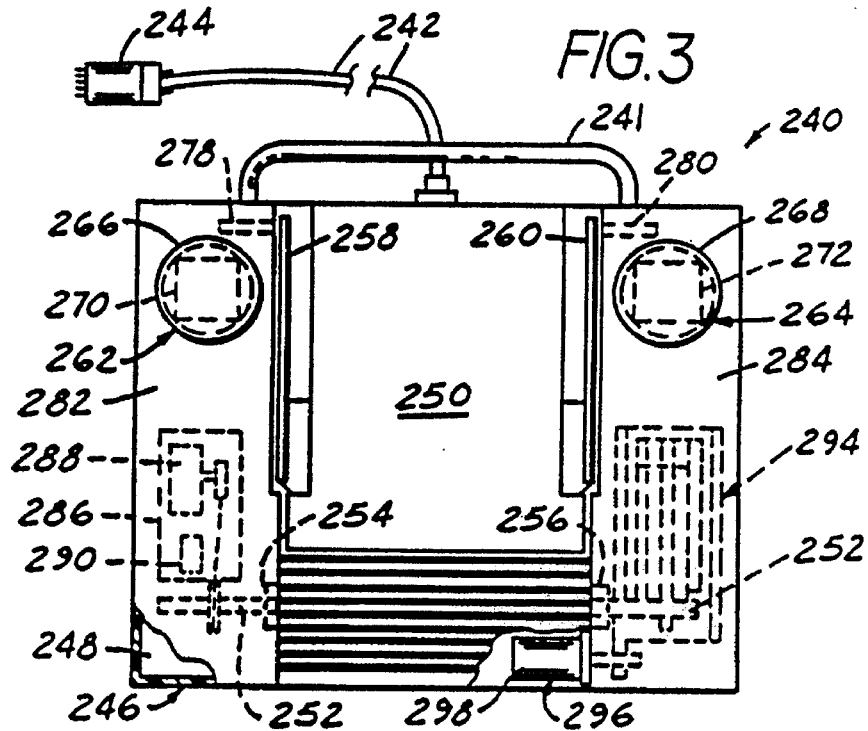
FIG. 3 is a plan view of the footswitch assembly usable with the present invention.

FIG. 3 shows a plan view of foot controller 240 (also called a footswitch assembly) utilized by the system 40 which has a metal carrying handle 241 and is linked directly to the console 46 with a suitable length of multi-conductor electrical cable 242 which has suitable multi-pin connector 244 at the end thereof that plugs into connector receptacle 190 on the back of the console 46. The footswitch assembly 240 includes: a large plastic molded housing 246 enclosed with a large rectangular bottom plate 248; having a footpedal 250 which pivots about a horizontal footpedal shaft 252 supported by sintered bronze flange bushing assemblies 254 and 256; left and right vertically arranged side pedals 258 and 260; and left and right top footswitch assemblies 262 and 264 having mushroom heads 266 and 268 and electrical contact blocks 270 and 272, shown in phantom, to signal when the respective top buttons have been pushed. Side switches 278 and 280, shown in phantom, which may be microswitches or magnetic proximity switches, are actuated and provide electrical signals indicating when their respective side pedals 258 or 260 have been pressed. The housing 246 includes left and right bunker structures 282 and 284 which rise above footpedal 250 upon which top footswitches 262 and 264 are mounted. Underneath left bunker 282 is located a footpedal position encoder assembly 286 shown schematically in phantom. Assembly 286 includes an optical position encoder 288 which produces two digital signals in a quadrature relationship as the shaft 252 rotates, and a zero reset switch 290. Under bunker 284 is located a detent assembly 294 which may be electrically engaged as desired via detent control solenoid assembly 296 including an electrical solenoid coil 298. The side switches 278 and 280 and top footswitches 266 and 268 provide on-off control of certain features during selected ophthalmic procedures. For example, the left top footswitch 266 provides on/off control of bipolar coagulation. The right top footswitch 268, via display 50 and buttons 52, may be configured to control the emergency rapid-up feature of the motorized IV pole option or to control some other operating room device via the accessory receptacle 194 on the back cover 166 of console 46. In anterior segment procedures, the footpedal is used to control irrigation, aspiration, phaco and vitrectomy modes in a manner like that used for the Storz DAISY console. However, the footpedal detents are new and are provided in the manner described in aforementioned application Ser. No. _____ to provide the surgeon with tactile feedback regarding the footpedal position. Further details of the construction and operation of the footpedal assembly 240 are given in aforementioned application Ser. No. _____ ───── entitled "Footswitch Assembly With Electrically Engaged Detents."

IV. Electronic Control System (FIG. 4)

A. General Overview of Electronics Hardware (FIG. 4A)

Figure 4A:
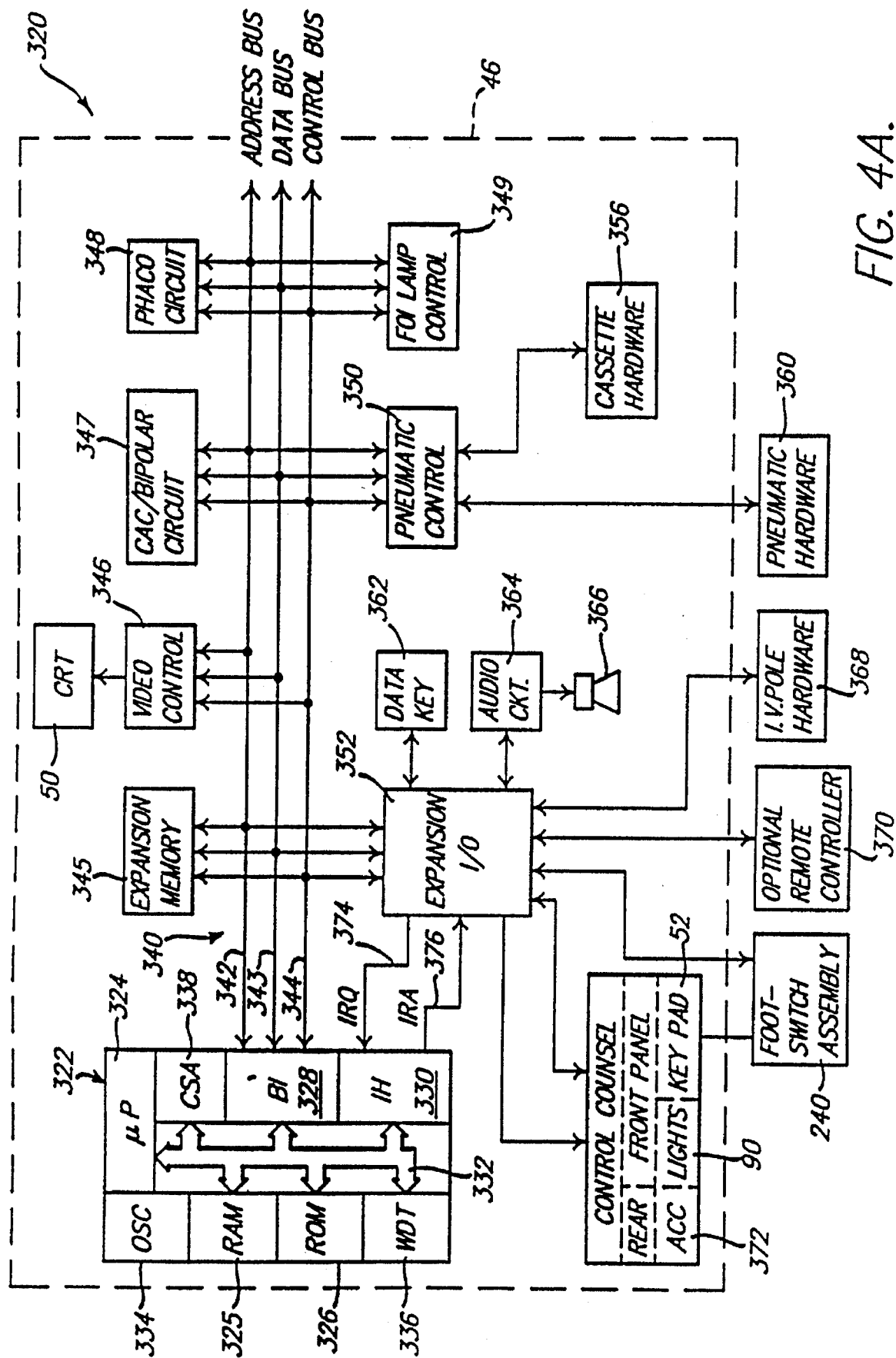
FIG. 4A is a simplified block diagram of the microprocessor-based electronic control system of the FIG. 1 control console showing how information is passed electronically between the microprocessor and the various boards and devices within the over-all surgical system.

FIG. 4A shows a simplified block diagram of a microprocessor-based electronic control system 320 found in the control console 46 shown in FIG. 1. Control system 320 includes a microcomputer 322 having a microprocessor 324, volatile (RAM) memory 325, nonvolatile (ROM) memory 326, a VME bus interface circuit or port 328, an interrupt handling circuit or port 330, and an internal control/address/data bus 332 which allows internal communications in conventional fashion between all portions of microcomputer 322. A preferred microprocessor 324 is a 68000 Series Motorola microprocessor with a clock speed of 12.5 Megahertz and one wait state for handling interrupts, although any other suitable microprocessor could be used. Computer 322 also includes a 25 Megahertz crystal oscillator 334, a watchdog timer circuit 336, and a chip select and addressing (CSA) section 338. The microcomputer 322 is located on a single board, called the processor board.

The microcomputer 322 which is located on its own printed circuit (PC) board, communicates with the remainder of the electronic control system 320 via a VME bus 340 consisting of address, data and control lines 342, 344 and 346. The VME bus 340 is used to communicate with seven other boards within the system 320, namely: the expansion memory PC board 345, the video control PC board 346 which drives the visual display SO, the CAC/bipolar circuit PC board 347, the phaco circuit PC board 348, the lamp control PC board 349, the pneumatic control PC board 350, and the expansion I/O PC board 352.

The groupings of various functions on distinct PC boards was done in order to make maintenance simpler. By clustering similar or related functions together on one board, it is possible to reduce diagnostic time and service costs since individual functions not performing correctly may be isolated on a board-by-board basis, and suspect boards may be replaced as needed. The processor board 322, the expansion memory board 345 and the video board 346 are all conventional purchased items from PEP Modular Computers GmbH of Kaufbeuren, West Germany. The manner in which all of these boards are designed and work from a hardware and operating system perspective is conventional. The manner in which the video board 346 drives the CRT 50 is conventional too. The CRT 50 used with the control console 46 is preferably a 9-inch diagonal monochrome monitor with standard resolution, although any other suitable two-dimensional display may be utilized such as liquid crystal display or electro luminescent display.

The lamp control board 349 is used to control the components in the lamp drawer 41 which is the source of light for fiber optic light pipe 100 shown in FIG. 1A. Pneumatic control board 350 is used to control the cassette hardware 356 and the pneumatic drawer hardware 360. The cassette hardware 356 refers to those input devices such as switches and output devices such as solenoids associated with the aspirant collection cassette 72 shown in FIG. 1A. The pneumatic hardware includes pressure transducer, a torque motor servo-valve and solenoids.

Expansion I/O board 352 is used to communicate or control the memory key circuit 362, the audio generator circuit 364, which drives speaker 366, the IV pole hardware 368, an optional remote controller 370, and the footpedal assembly 240 of FIG. 2. The expansion I/O board 352 also is used to interrogate or operate various other input and output devices associated with the control console 46, such as the keypads 52, the indicator lights on secondary panel 60 and connector panel 90 and the accessory relay 372 associated with accessory receptacle 194 shown in FIG. 1A. All user-generated input commands are handled through I/O board 352. To ensure such commands are promptly communicated to the processor 324, board 352 generates an interrupt request (IRQ) signal on line 374 to inform the processor 324 that the I/O board needs to be serviced. The processor also generates an interrupt acknowledge (IRA) signal on line 376. In this manner, user input commands take precedence over lower priority I/O tasks also being handled via VME bus 340.

B. CAC/Bipolar Circuit (FIG. 4B)

Figure 4B:
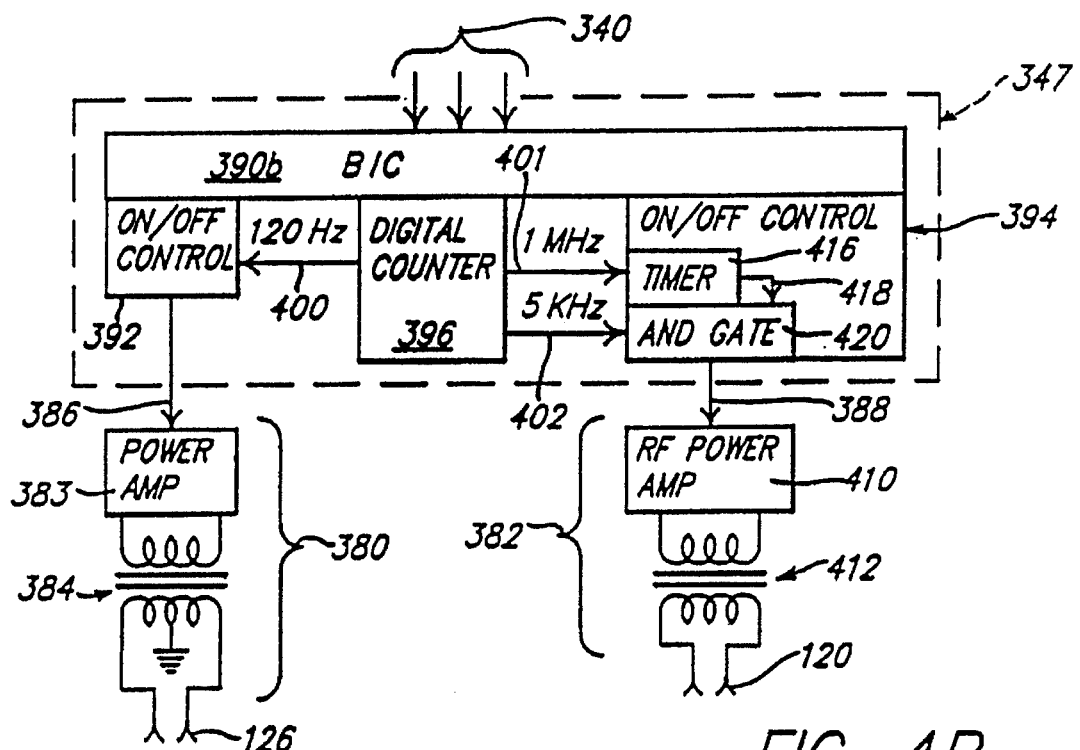
FIG. 4B is a detailed block diagram of the operation of the CAC/bipolar board and equipment of the FIG. 1 control console.

FIG. 4B is a detailed block diagram of the CAC/bipolar circuit board and the power amplifier/transformer sections 380 and 382 which it drives with DC level control signals 386 and 388. The board 347 includes a standard VME bus interface circuit (BIC) 390b, which is interfaced directly to on/off control circuits 392 and 394 and to a multi-stage digital counter 396. The digital counter 396 is continuously run, and taps are provided at various stages thereof to provide three digital logic level, timebase signals, all of which are square waves having a 50% duty cycle, namely a 120 Hz signal on line 400, a 1 MHz signal on line 401 and a 5 KHz signal on line 402.

CAC function is best understood by explaining a few basics about the capsular anterior capsulotomy procedure. During this procedure, a pyramidally-shaped tip positioned at a right angle to and near the tip of a microsurgical needle vibrates at a fixed rate, such as 120 Hz, in two dimensions, namely axially and transversely. This cutting action is used to cut the anterior capsule of the eye, Upon receiving an appropriate command from the processor 324 over the VME bus 340, on/off control 392 allows this signal 400 to pass through to line 386. Power amplifier 383 amplifies digital signal 386 to approximately 2 watts and transformer 384 converts the output signal from the power amp 383 to a square wave which varies between plus and minus 3.5 volts. The amplitude and frequency are fixed. The power from the secondary transformer 384 is applied to connector 126 on receptacle panel 90 of the console 46. A conventional CAC probe from Storz may be plugged into connector 126.

The bipolar cautery function implemented by the board 347 is conventional, and has been used in the Storz DAISY console several years. In bipolar cautery, a high frequency moderate power signal is applied to electrodes located at the tips of a conventional bipolar probe. The high frequency electrical signal is used to cauterize severed blood vessels, incisions and the like. In the preferred embodiment, a 1 MHz power RF signal is output to connection 120 by RF power amplifier 410 and step-up transformer 412. The maximum output may be limited to 7.5 watts at 100 ohms. The power of the RF signal applied to connector 120 is preferably adjustable from zero to 100 percent. In the electronic control system 320, this is implemented in the following manner, First, the bipolar signal applied to connector 120 is considered to be at 100 percent power when the RF signal is modulated so as to be on 50 percent of the time and off 50 percent of the time. The low level 1 MHz signal 401 is pulse width modulated by on/off control 394 using the 5 KHz signal 402 as a time base. The signal 402 has a 50 percent duty cycle, which means it is on for 100 microseconds and off for 100 microseconds each cycle. This represents 100 percent bipolar power. To reduce the power level, a digital timer circuit 416 within the on/off control 394 reduces the on time of signal 402 while increasing the off time, thus resulting in a pulse width modulated (PWM) signal 418 having a duty cycle corresponding to the duty cycle required to achieve the desired power level. This signal 418 is applied to gate circuit 420 resulting in signal 388 being a PWM composite RF signal which when on oscillates at 1 MHz. Signal 388 is fed to RF power amplifier 410, whose output drives the primary of transformer 412. Transformer 412 isolates the amplifier 410 and provides proper output impedance levels at its secondary. On/off control block 394 thus regulates when the composite RF signal 388 is on, and its effective duty cycle.

C. Phaco Calibration & Drive Circuit (FIG. 4C.)

Figure 4C:
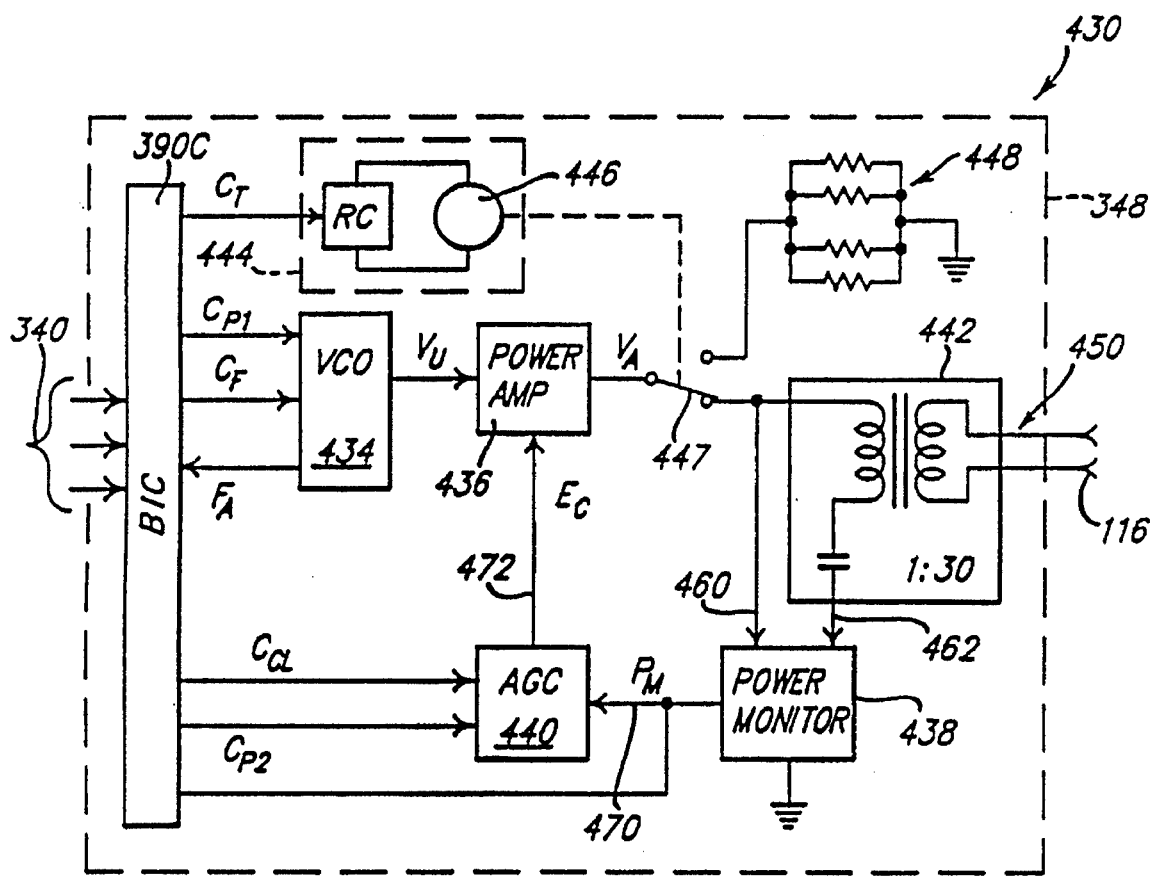
FIG. 4C is a detailed block diagram of the calibration and drive system for a phaco probe.

FIG. 4C shows a detailed block diagram for the phaco circuit 430 forming pad of electronic control system 320. The phaco circuit includes another standard VME BIC 390c, which is used to produce a variety of digital control signals including the test command signal $CT_T$ a first power command signal $Cp_{P1}$ a closed loop command signal $C_{CL}$ and a second power command signal $C_{P2}$. The phaco control module includes a voltage controlled oscillator (VCO) section 434, a power amplifier section 436, a power monitor section 438, an automatic gain control (AGC) section 440, a transformer section 442, a relay control section 444 including relay coil 446 which operates a Form-C electrical contact 447 and a resistor bank 448. The phaco drive circuit 430 produces an ultrasonic (US) signal 450 which ranges in strength between 0 and 35 watts at a frequency in the range of 26 KHz to 31 KHz at approximately 5 kilo-ohms. This ultrasonic signal is applied to connector 116 of the receptacle panel 90 of console 46. A conventional phacoemulsification or phaco fragmentation probe may be provided power by plugging its electrical jack 114 into receptacle 116.

In operation, the phaco drive circuits 430 checks itself by having relay section 444 switch the contact 447 to its opposite position, thus applying the US signal from power amplifier 436 to resistor bank 448. Next, circuit 430 switches relay coil 446 off, thus allowing power to flow from amplifier 436 through contact 447 to transformer section 442. At this time the dominant resonant frequency of the ultrasonic transducer is determined by monitoring the voltage and currents signals on conductors 460 and 462 as a US test signal VA is swept through frequencies within the range of 26 KHz to 32 KHz. During this time, processor 324 looks for power peaks, among other things, to find the resonant frequency. Once the dominant resonant frequency of the transducer/probe plugged into connector 116 is determined, the phaco drive circuit 430 enters a drive mode. In this mode, the circuit 430, under user commands interpreted by processor 324 and delivered via VME bus 340, drives the VCO section 434 at the dominant resonant frequency and desired power level indicated by commands CF and $C_{P1}$, which is passed along as a voltage signal $V_u$ to power amplifier 436, where it is amplified and transferred as signal $V_A$ to transformer section 442. Power monitor section 438 observes the voltage and current applied to the primary of transformer section 442, and produces the monitored power signal $P_M$ on line 470, which feeds into AGC section 440 where it is compared against the desired power command $C_{P2}$. Any deviation between the power desired and the monitored power results in a non-zero error correction signal $E_c$ on line 472, which alters the gain of power amplifier 436 to compensate for and eliminate this error. In this manner, constant power operation of the ultrasonic transduce/probe combination plugged into receptacle 116 is assured. Further details of the operation of phaco drive circuit 430 are set forth in aforementioned application Ser. No. _____ entitled "Control System For Calibrating And Driving Ultrasonic Transducer."

D. FOI Lamp Control Circuit (FIG. 4D)

Figure 4D:
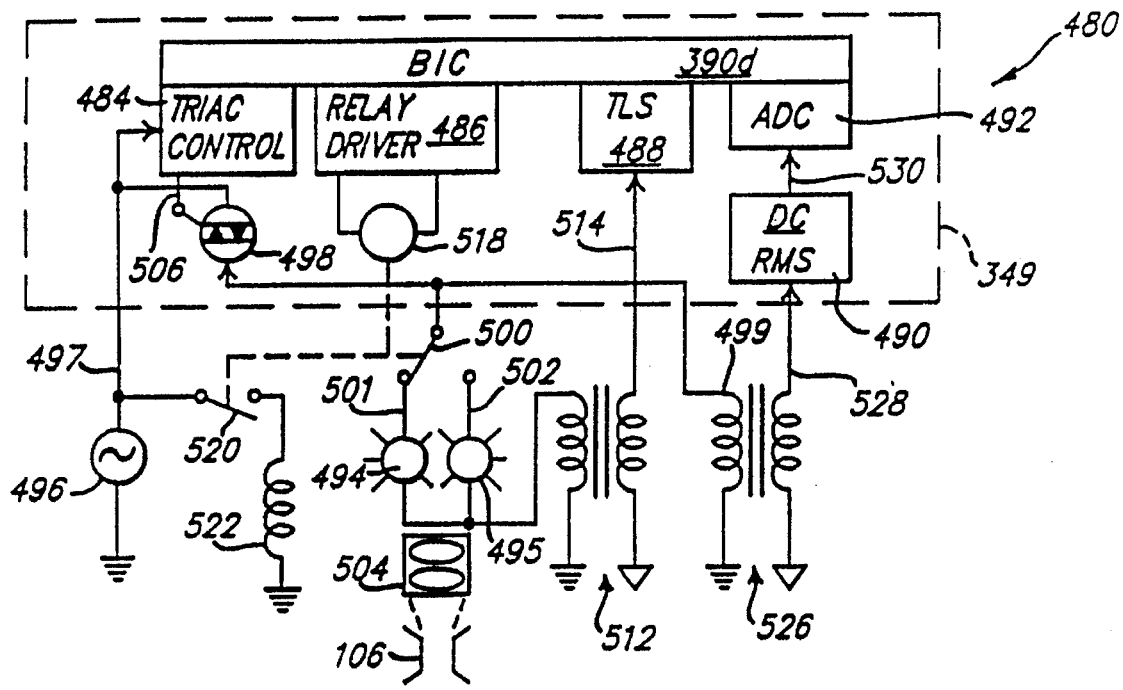
FIG. 4D is a detailed block diagram of the illumination lamp control circuitry and electrical hardware associated therewith.

FIG. 4D shows a block diagram of the fiberoptic illumination (FOI) lamp control circuit, which includes the lamp control board 449 shown in FIG. 4A, and the electrical hardware 480 controlled by PC board 349. The board 349 includes a triac controller 484, a relay driver circuit 486, a threshold level sensing (TLS) circuit 488 an RMS-to-DC converter 490 and 8-bit resolution analog-to-digital converter (ADC) 492. Conventional optoisolators are used in circuits 484 and 486 to help prevent electrical noise for these two circuits from being passed to other parts of the electronic control system 320.

The lamp drawer 41 (see FIG. 1A) includes two lamps 494 and 495 shown in FIG. 4D which are powered by a low voltage (15 volts RMS) AC signal source 496 which has its power delivered via conductor 497 to triac 498, conductor 499, Form-C relay contact 500 and then to conductor 501 or 502. During normal operation, the primary bulb 494 is employed to illuminate through a conventional focusing lens 504 receptacle 106 of front panel 90. Processor 324 provides signals via VME bus 340 to the lamp control board 449 instructing triac controller 484 as to how brightly to turn on the light bulbs 494 or 495. This is accomplished in conventional manner by the timing of the gate signal on line 506 applied to triac 498.

Isolation transformer 512 is used to monitor the light bulb current to determine if the lamp circuit is operating properly. Current passing through either bulb 494 or 495 also passes through the primary of transformer 512, causing a voltage to be developed across its secondary which is delivered by conductor 514 to TLS circuit 488, which produces an output when the sense current exceeds a predetermined threshold level. Processor 324 periodically checks to see if the output of TLS circuit 488 is on, which indicates that the bulb circuit is operating satisfactorily. If this signal should be absent, relay driver 486 energizes relay coil 518 which transfers the Form-C contact 500 so that power from triac 498 is delivered via conductor 502 to the second light bulb 495. In this manner, lamp driver circuit 480 automatically switches to the secondary lamp source 495 when the primary bulb 494 fails to operate for any reason. At the same time, electrical contact 520 closes and rotation solenoid 522 causes a mirror (not shown) to rotate into position so that light from secondary bulb 495 shines directly into focusing lens 504.

Isolation transformer 526 monitors the voltage on line 499, which is equal to the voltage applied across the light bulb. This voltage signal induces a corresponding current in conductor 528 connected to RMS/DC converter 490 which produces a DC signal on line 530 proportional to the amplitude of the signal on line 528. ADC 492 converts this into a digital value which is transferred via BIC 390d and VME bus 340 to processor 324. Processor 324 periodically examines this value to determine whether fluctuations in the applied voltage level of the bulb are occurring. If they are, processor 324 issues appropriate compensating commands to triac controller 484, thus keeping the effective power applied to the light bulbs constant, to help ensure a constant level of illumination in accordance with the illumination level setting selected by a user via keys 52.

E. Electrical Circuit For Pneumatics System (FIG. 4E)

1. Pneumatics Control Circuit

Figure 4E:
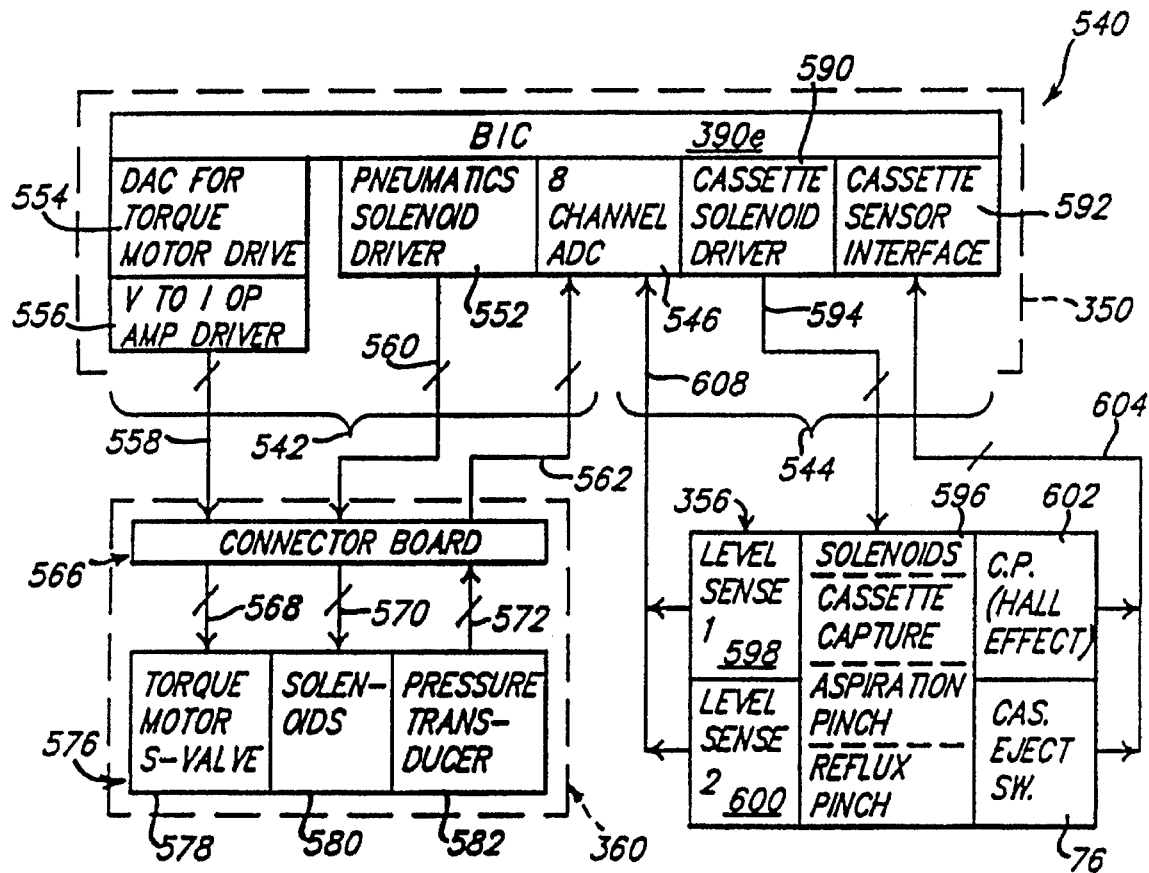
FIG. 4E is a detailed block diagram of the pneumatics control and cassette control circuitry and related electrical equipment found in the pneumatic system and cassette system of the FIG. 1 console.

FIG. 4E is a block diagram of the electrical control circuitry 540 found on pneumatic control board 350, which as shown in FIG. 4A is used to drive the electrical devices forming pad of the cassette hardware 356 and the pneumatic hardware 360. The circuitry 540 includes a pneumatic control section 542 and a cassette control section 544. The BIC 390e and an 8-channel ADC 546 are common to both sections. Pneumatic control section 542 include a solenoid driver circuit 552 and a DAC 554 and a voltage-to-current op amp driver circuit 556. Three sets of conductors 558, 560 and 562 deliver signals from section 542 to a common connector board 566 located at the pneumatics drawer 44. Connector board 566 serves as a convenient termination point for three sets 568, 570 and 572 of internal conductors which run between connector board 566 and the actual electrical devices 576 being driven or read. The devices 576 include a torque motor servo valve 578 and set 580 of solenoids which operate valves and a set 582 of pressure transducers. The torque motor servo valve 578 is used to provide a proportionally metered flow of pressurized air which is used to create a desired level of vacuum for aspiration or of air pressure for operating microscissors. The rate of air flow is proportional to the opening in the valve, which is proportional to the electric current supplied to the torque motor valve 578. Processor controls this current level by sending appropriate control signals over VME bus 340 to the BIC 390e in board 540 which causes DAC 545 to generate a specified voltage level. This voltage level is converted by op amp driver 556 into an amplified current signal passed along conductors 558 and 568 to servo valve 578. Processor 324 also controls the operation of solenoid valves in the pneumatic system 44 by sending appropriate signals to BIC 390e shown in FIG. 4E, which turns on individual driver circuits, as desired in solenoid driver's circuitry 552. Thus suitable voltage signals (such as 12 volts DC) are applied along individual ones of conductors 560 and 570 to turn on desired ones of the solenoids 580.

Pressure transducers 582 generate low voltage analog signals which are routed up through conductors 572 and 562 to respective individual channels of ADC 546, which read the analog signal levels. Processor 324 polls ADC 546 periodically through BIC 390e to obtain digital values of the pressures sensed by transducers 582. Further details about the construction and operation of the pneumatics hardware 360 and operation of the pneumatic system are provided below.

2. Cassette Control Circuit

Cassette control section 544 includes conventional solenoid driver circuitry 590 and sensor interface circuitry 592. Solenoid drive circuit 590 provides amplified voltage signals to three solenoids used to operate two position, three-way pneumatic valves that individually control three small pneumatic cylinders used for cassette capture, aspiration pinch and reflex pinch operations. The cassette hardware 356 includes two level sensing devices 598 and 600 which detect when fluid in the collection cassette 72 has reached predetermined levels one and two corresponding to "cassette nearly full" and "cassette full" fluid levels. Hardware 356 also includes a Hall effect switch 602 (used to detect the presence of the spring-loaded mechanical lever which is pressed when the collection cassette 72 is fully inserted in slot 70) and the cassette eject switch 76 shown on panel 190 in FIG. 1A. Sensor interface 592 reads the electrical signals on conductor 604 to determine the states of devices 602 and 76. Two channels of ADC 546 read the states of level sensing devices 598 and 500 over conductors 608. Periodically, processor 324 interrogates sensor interlace 592 and ADC 546 to determine the status of sensing devices 598, 600, 602 and 76. The level sensing device 598 preferably consists of a LED and phototransistor positioned on opposite sides of the cassette 72. As the liquid level rises, a plastic ball which floats rises as well and breaks the light beam between the LED and phototransistor. The level sensing device 600 preferably consists of the same type of LED/phototransistor arrangement, but located at a slightly higher level. Further details about the cassette hardware 356 is provided in aforementioned application Ser. No. _____ entitled "Remote Control Console For Surgical Control System."

F. Expansion I/O Board Circuit (FIG. 4F)

1. Introduction

Figure 4F:
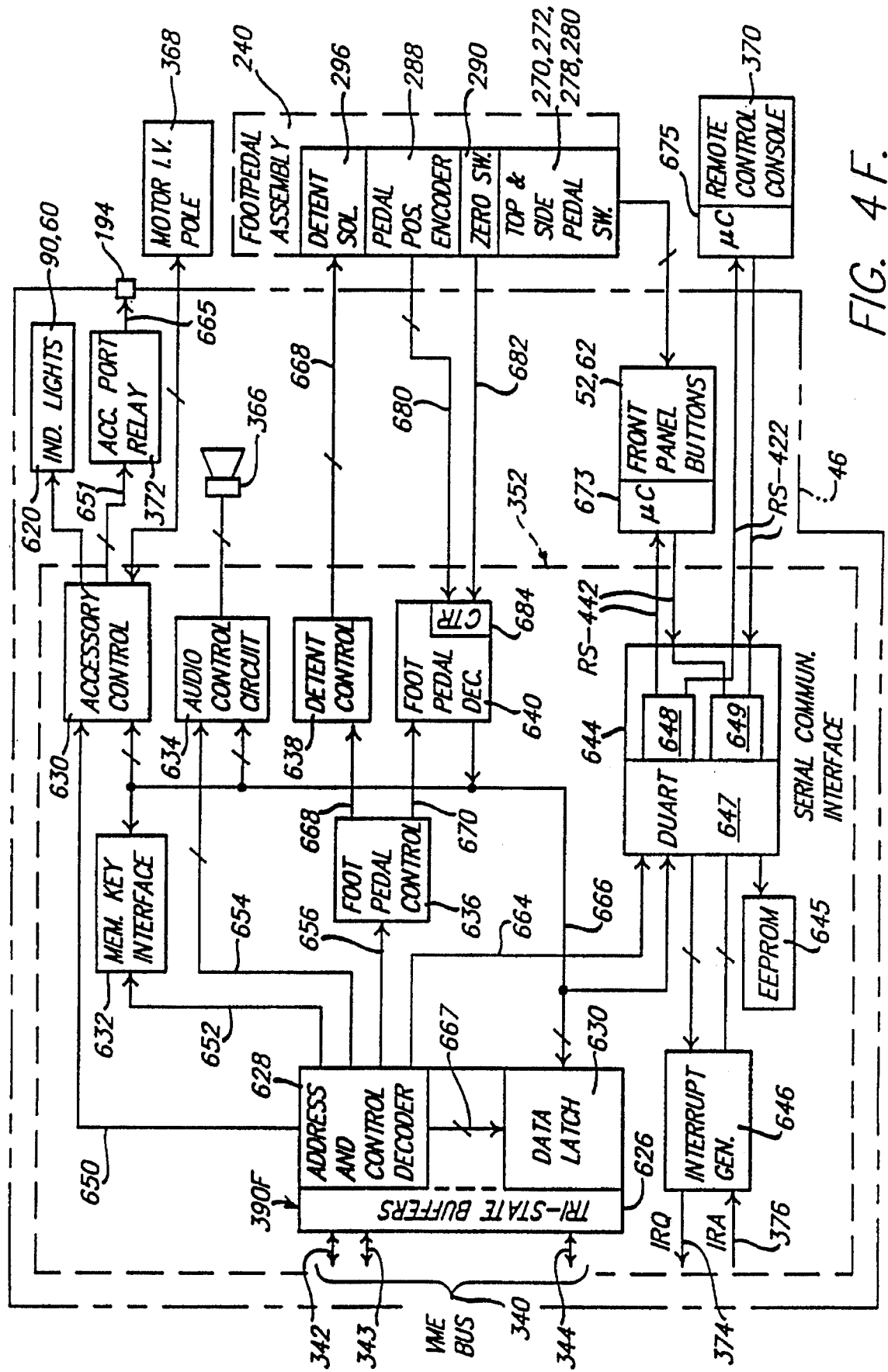
FIG. 4F is a detailed block diagram of the I/O expansion board shown in FIG. 4A and the electrical equipment interfaced therewith.

FIG. 4F shows a detailed block diagram of the I/O expansion board 352 and the devices which it drives or reads, namely: the indicator lights on secondary front panel 60 and on connector panel 90 (represented by block 620) and relay 372 for accessory connector 194, the speaker 366, and the primary and secondary front panel buttons 52 and 62, all of which are located in or on the control console 46 (indicated by these devices being to the left of the dashed line 46, which represents the perimeter of control console 46). The board 352 also drives and/or reads devices in the motorized IV pole assembly 368, the footpedal assembly 240, and the optional remote control console 370, which are all outside of the control enclosure 46.

The I/O board 352 communicates with the VME bus 340 through a VME interface 390f which includes tri-state buffer circuits 626, address and control decoder circuit 628 and 16-bit data latch or register 630. The I/O circuitry on board 352 also includes four primary control interface circuits, namely accessory control 630, memory key control 632 for memory key 132, audio control 634 for speaker 366, and footpedal control 636. Control circuit 636 in turn directs the operation of two slave circuits, namely detent control 638 and footpedal decoder 640 which actually communicate with devices in footpedal assembly 240. Board 352 also includes a conventional serial communications interface circuit 644 which drives and reads in conventional fashion an interrupt generator circuit 646 and a non-volatile memory 645, which preferably is an electrically erasable programmable read only memory (EEPROM). Circuit 644 includes three conventional integrated circuit (IC) chips, namely a dual universal asynchronous receiver/transmitter (DUART) 647, a dualchannel RS-422 transmitter chip 648, and a dual-channel RS-422 receiver chip 649, all functionally connected as shown in FIG. 4F.

The primary interface circuits 630–638 and the serial communications interface 644 communicate with VME bus interface 390f via control signals passed along dedicated control lines 650–656 and 664. Data to be sent to and/or received from circuits 630–638 or communications interface 644 is passed along an internal 16-line data bus 666 connected to data latch 630. Footpedal control 636 communicates with slave circuits 638 and 640 via lines 668 and 670. Each of the primary control circuits and the communications interface 644 contains a data latch circuit for receiving, holding and/or transmitting data to internal data bus 666.

Address and control decoder 628, upon receipt of commands from processor 324 via VME bus 340, decodes the command and address signals on lines 342 and 343, and in accordance with the decoded instructions distributes the desired control signals and/or via lines 667 commands data signals to the control interface circuit 630–636 or 644 which the processor 324 desires to address. The control interface circuits 630–636 have no intelligence and do not on their own seek to communicate with processor 324. Instead, processor 324 just periodically writes or reads data to these control circuits.

2. Functions of Serial Communications Interface 644

The communications interface 644 has two devices connected to it which have intelligence, namely microcontroller 673 associated with the two front panels 48 and 60 on console 46 and microcontroller 675 associated with optional remote controller 370. Serial communications interface 644 converses with the microcontrollers 673 and 675 using the well-known RS-422 communications protocol at a suitable data rate, such as 9600 baud. Whenever either of these two microcontrollers has information to be sent to processor 324, it serially sends a byte of information to the communications interface 644 which in turn automatically causes an interrupt to be generated. Communications interface 644 is identified as the source of the interrupt, the interrupt is acknowledged via line 376, and the processor 324 causes data serially communicated to the DUART 647 by the microcontroller to be loaded into the data latch 630, and then via VME bus 340 reads the data from latch 630 in one of its next I/O cycles.

Microcontroller 673 has its own internal oscillator and micro program. It continuously monitors all of the buttons 52 and 62 found on front panels 48 and 60 of the control console 46 to determine whether they have been depressed. The buttons are electrically arranged in a matrix of row and columns, and by interrogating each position of the matrix the state of all the buttons is determined. The microcontroller advises the processor whenever a button is pressed, and keeps periodically advising the processor 324 of this fact for as long as the button remains pressed. Microcontroller 673 also monitors, as pad of the aforementioned matrix of buttons, the status top buttons 270 and 72 and side pedals switches 278 and 280 within the footpedal assembly.

The microcontrollers 673 and 675 are provided in order to ensure that the main processor 324 is apprised of changes in status at the front panel console or remote control console virtually immediately for a very quick response to operator requests. In other words, all the routine functions which need not be performed quickly by the main processor 324 are made to wait while processor 324 responds to an interrupt and reads the data from the microcontroller and puts it into a table in main memory 325 one byte at a time. In main memory, a table listing the states of all the buttons on the main console and the remote control console is kept. The microcontrollers 673 and 675 only advise the main processor 324 of changes in the state of any of the buttons. In this manner, communications between the microcontrollers 673 and 675 are handled far more efficiently than updating the entire table each time an interrupt is generated. Microcontroller 675 operates in the same manner as microcontroller with respect to the matrix of buttons it monitors. The remote control console 370 also contains a keyboard interface circuit almost identical to interface circuit 680. This interface circuit is described in detail in application Ser. No. _____ entitled "Remote Control Console For Surgical Control System."

Communications interface 644 also reads and writes data to EEPROM 645 in conventional fashion. EEPROM 645 is provided so console 46 can store, in a non-volatile manner, any user-programmed default values, configuration codes, calibration data and/or any other pertinent parameters which may be entered in by the user.

3. Accessory Control Circuit 630

The accessory control 630 contains: a plurality of memory latches and indicator light driver circuits dedicated to driving the indicator lights 620 on connector panel 90 and secondary panel 60; a plurality of memory latches, relay driver circuits, sensing circuits and an optical position decoder, all of which are dedicated to sending control signals to and receiving information from motorized IV pole hardware 368; and a latch and relay driver for operating relay 372. When a relay driving signal is applied to line 662, relay coil 372 is energized, which closes a normally open contact and thus completes the circuit available on lines 664 connected to the connector receptacle 194 shown in FIG. 1B. The details of the electrical devices and circuits in the motorized IV pole 368 are described in application Ser. No. _____ entitled "Motorized IV Pole Assembly," and thus need not be described here.

4. Audio Control Circuit 634

The audio control circuit 634 is of standard design, and uses a conventional programmable sound generation circuit on a large scale integration (LSI) chip to produce the various tones at various amplitudes used to indicate device operation and provide audio error signals to the console user. The output signal from this chip drives a separate conventional low-power audio amplifier chip, whose output is connected to and drives speaker 366. A suitable sound generator is available from Microchip Technology, Inc. of Chandler, Ariz. as Model No. AY8930. One of the unique features provided by control console 46 is the user of select various tones and amplitudes for the selected tones to represent different conditions or states that the control system 40 may be placed in by the surgeon. A further description of this aspect of the control system 40 is provided in aforementioned application Ser. No. _____ entitled "Control System For Ophthalmic Surgical Instruments."

5. Footpedal Control Circuits 636–640

In accordance with commands from footpedal control 636, the detent control 638 provides positive and negative 24 volt DC power signals on lines operate the detent solenoid 698. A momentary +24 VDC signal extends the armature of solenoid 698 while a momentary –24 VDC signal causes it to retract. Conventional magnetic and/or mechanical detents built into solenoid 698 hold its armature in the last position the signals on lines 668 placed it in.

Footpedal decoder 640 receives low-voltage quadrature signals over conductors 680 from encoder 288, and a low-voltage digital signal on line 682 from zero switch 290. Switch 290 is released whenever footpedal 250 is moved more than two degrees from its spring-returned position, that is, the position pedal 250 is in when it is not pressed at all. When the signal on line 682 is in its reset state, bi-directional multiple stage digital counter 684 within decoder circuit 640 is held in a reset state. As soon as signal 682 goes to its opposite state, counter 684 is allowed to operate under the control of the quadrature signals on lines 680 which increment or decrement the counter with each pulse. Thus the accumulated count in counter 684 reflects the true angular position of footpedal 250. Processor 324 periodically (once every 50 milliseconds) reads the value in counter 684 by sending appropriate control signals to bus interface 390ƒ so that counter 684 can send its present count to data bus 666, where it is held by latch 630 until read by the processor 324 via VME bus 340.

The status of top button switches 270 and 272 and the side pedal proximity switches 278 and 280 of the footpedal assembly 240 are also read through microcontroller 673, which as previously explained serially transmits information to communications interface 644, through internal bus 666, bus interface 390ƒ and VME bus 340 to processor 324.

V. The Details Of Pneumatic System 43

A. Schematic Diagram of Pneumatic System (FIG. 5)

Figure 5:
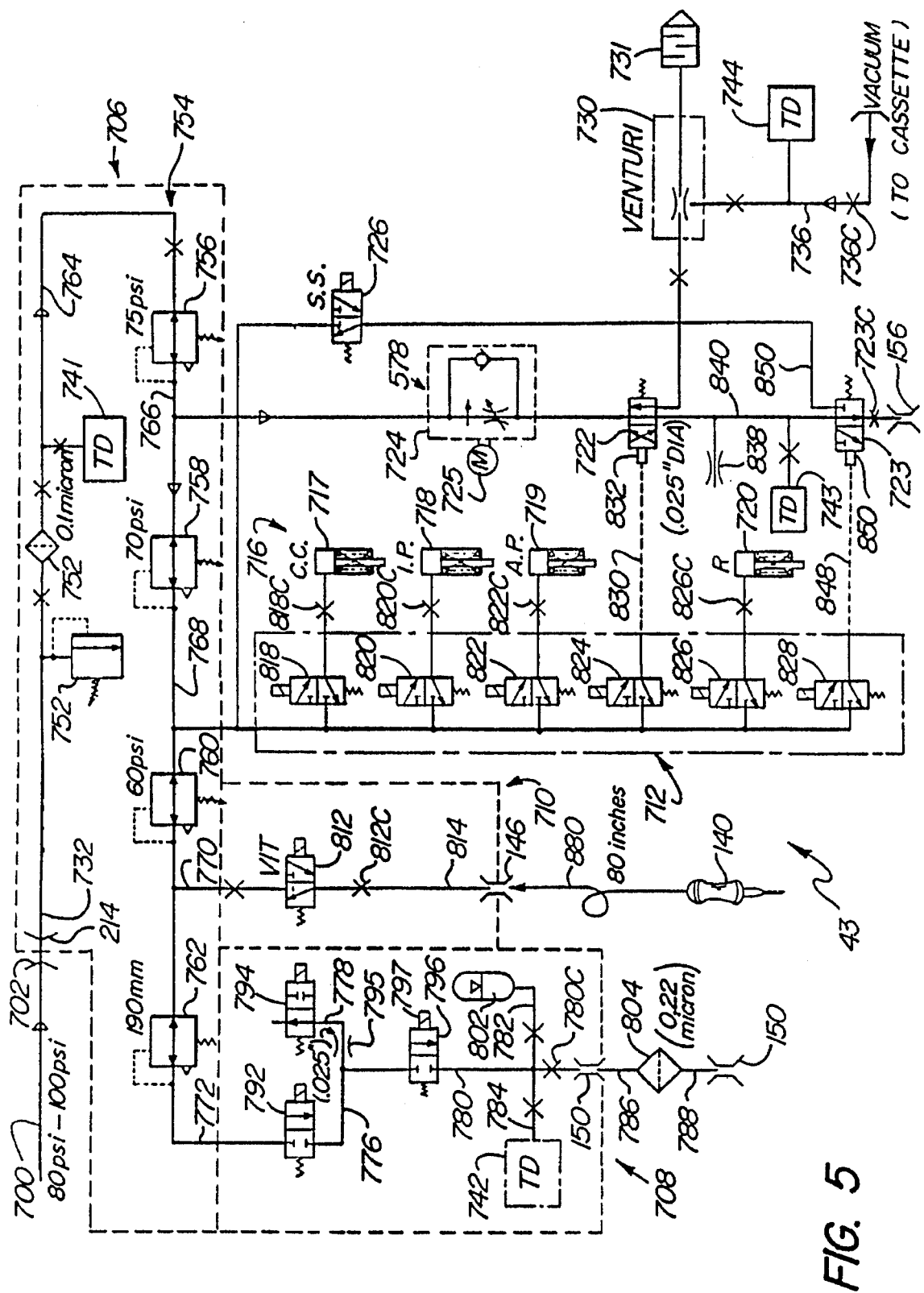
FIG. 5 is a detailed schematic diagram of the pneumatic control system which includes the improvements of the present invention.

FIG. 5 is a detailed pneumatic schematic diagram of the pneumatic control system 43 of the present invention. All of the components, except for the supply line 700 and Schrader quick-disconnect coupling 702 shown in the upper left-hand corner of FIG. 5 are located within or on the drawer 44, which as shown in FIG. 1A, is located at the back right side of the console 46. The pneumatic system 43 includes an air pressure regulator section 706, an IOP system 708, a vitrectomy cutter control circuit 710, a solenoid valve manifold section 712 with six valves which control a set 716 of four springreturned pneumatic cylinders 717–720 and two pilot operated valves 722 and 723; a proportional servo valve 578 including valve body 724 and a torque motor operator 725, a high-speed solenoid valve 726, and an air-to-vacuum conversion means namely venturi 730 with exhaust muffler 731.

The system 43 has only one pneumatic input source which is through the hospital grade Schrader quick-disconnect coupler 214 connected to an internal main supply line 732. Any suitable source of pressurized, filtered, dry gas suitable for surgical use such as air or nitrogen may be provided to the system 43, such as by a hospital air supply system or by a pressurized storage tank. The system 43 requires that supply input pressure be at least 80 psig and is preferably no more than 100 psig. The system 43 only has four fluid outlet ponds which extend to the perimeter of console 46. Only eight outlet lines extend outside of drawer 44. The four outlet ponds which extend to the console perimeter are routed by flexible tubing to the cassette area of connector panel 90, where they are attached to and become part of the vitrectomy connector 146 from the vitrectomy control circuit 710, at the IOP connector 150 from the IOP system 708, the scissors connector 156 from the second pilot-operated valve of set 718, and the aspiration connector 734 which extends from the air-to-vacuum converter 730 via pneumatic tubing line 736. The four lines constitute four of the eight outlet lines which extend outside the drawer 44. The remaining four outlet lines go to the air-actuated springreturned cylinders 716–720. The system also includes a set 582 (see FIG. 4E) of four pressure transducers 741, 742, 743 and 744 which each generate an analog electrical signal having a magnitude proportional to the pressure (or vacuum) it senses. As will be described later a spare transducer 745 (not shown in FIG. 5) may also be provided in drawer 44.

B. The Pressure Regulation Section 706

Section 706 includes: a conventional main pressure relief valve 750 preferably set to 125 psig to protect against air supply overpressure conditions; a very fine gauge filter assembly 752 with a replaceable submicron filter cartridge (0.1 micron filter preferred); the pressure transducer 741; and a set 754 of pressure regulator valves 756, 758, 760 and 762 arranged in series as shown and preferably set respectively to 75 psig, 70 psig, 60 psig and 190 mmHg. Pneumatic tubing 764 extends from the filter 752 to the main pressure regulator 756. Pneumatic lines 766, 768, 770 and 772 respectively extend from the downstream side of regulators 756, 758, 760 and 762 to other sections of system 43. If desired, the pressure regulating means 750–762 may be of the adjustable type or may be of fixed pressure rating type. If of the adjustable type, they are preferably adjusted to the desired pressure setting when system 43 is first assembled and tested, and then their adjustment screws locked tight before being put into surgical use.

C. IOP System 708

The IOP system 708 includes pneumatic lines 776–788 and three two-way, two-position solenoid-operated control valves, namely valves 792, 794 and 796. The system 708 also includes an accumulator 802, a submicron filter 804 and the pressure transducer 742. The submicron filter 804 is normally provided as pad of the disposable tubing set used by ophthalmic surgeons. The purpose of the IOP system, as previously explained, is to provide a precisely controlled supply of low flow, low-pressure air, which is required in certain ophthalmic posterior segment surgical procedures, or can be used to pressurize a bottle of irrigating solution also often used during ophthalmic surgery. The maximum pressure that can possibly be delivered by the IOP system is set by regulator 762, which can be raised or lowered as desired by adjusting the regulator. By itself, a spring-loaded mechanical regulator, such as regulator 762, is not capable of providing the fine and readily adjustable control of low-flow, low air pressure desired from an IOP system. In an operating room setting, it is highly desirable to allow the pressure produced by an IOP system to be adjusted via an easily actuated electrical knob or switch. This requires an electrical interface to the pressure adjustment mechanism of the IOP system. To reduce manufacturing costs, the present invention uses solenoid valves 792–796 in combination with accumulator 802 to achieve precision adjustment of IOP pressure. Via transducer 742, the IOP output pressure at connector 150 is monitored on line 780, and solenoid valve 792 and 794 are cycled as will be explained below, to obtain the desired level of pressure.

The IOP system 708 employs the accumulator 802 to smooth out any pulses on the line 780, while the submicron filter 804 ensures that contaminants do not enter the surgically used air stream provided by IOP system 708 via connector 150.

The valve 792 is called the IOP charge valve, since it allows pressure to build up in the IOP system, while the valve 778 is called the IOP exhaust valve, since it allows pressurized airs to flow through metering orifice 795 to atmosphere, thus depressurizing the IOP system. Valve 796 is called the IOP shut-off valve since only when its solenoid 797 is energized is air able to flow from the pressure source (i.e., line 772) through to connector 150. The size of the opening in fixed orifice 795 is selected to be approximately one-half the size of the passageway through the valve 792 and through the valve 794.

The IOP system has five distinct control states or modes, which depend upon the status of the vanes 792–796, and which are listed in Table 1 below.

TABLE 1

MODES OF IOP SYSTEM 708
VALVE FUNCTION AND STATE

| Mode No. | Mode Name | Charge Valve 792 | Exhaust Valve 794 | Shut-off Valve 796 |
|---|---|---|---|---|
| 1 | exhaust | closed | opened | opened |
| 2 | fast charge | opened | closed | opened |
| 3 | slow charge | opened | opened | opened |
| 4 | hold | closed | closed | opened |
| 5 | power-off | closed | opened | closed |

In the first mode, also called the "exhaust" mode, charge valve 792 is closed and exhaust and shut-off valves 794 and 796 are opened. This allows all pressure above atmospheric to escape through metered orifice 795 and exhaust valve 794. In the second or "fast charge" mode, charge valve 792 is opened and exhaust valve 794 is closed, while the shut-off valve 796 remains opened. In this mode, pressure builds in lines 776–788 at a maximum rate allowed by the size of the components and lines. The third or "slow charge" mode has all three valves 792–796 opened. In this mode, roughly half of the incoming pressurized air on line 772 is able to escape directly to atmosphere via opened valve 794. Thus the rate of increase of air pressure is significantly slower than in the fast charge mode. When the air pressure in line 780 finally reaches the desired level, the system 708 enters its fourth mode, which may be called the "hold" mode. Valves 792 and 794 are closed while shut-off valve 796 remains opened. If the desired air pressure level should be above the actual air pressure level by some margin (e.g., 2 mmHg or more), this will be sensed by transducer 742 and processor 324 will place system 708 in the exhaust mode to reduce the air pressure.

The fifth or "power-off" mode is really an uncontrolled state where all electrical power to the IOP system 708 (or at least to its solenoid valves 792–796) is turned off or otherwise lost. For example, in the event of a power failure, IOP system 708 and its electrical devices will be immediately de-energized. In this "power-off" mode, valve 796 closes, which helps preserve pressure in lines 780–788 for as long as the charge in the accumulator remains. Eventually the pressurized air in lines 780–788 may leak out through the pneumatic lines connected to connector 150. For example, if a posterior segment procedure was in progress during a power failure, eventually the stored air pressure or charge in lines 780–788 and accumulator 802 may leak out if the seal in the eye is less than perfect. In such a situation, the IOP system 708 of the present invention has the advantage of maintaining the intraocular pressure in the eye for a greater length of time in comparison to previous systems which, upon power failure, automatically bleed down the IOP pressure lines. In such a prior art system, if an accumulator is provided at all, it is located on the upstream side of a valve that closed upon power failure, which allowed the accumulator to bleed out upon electrical power outage. In contrast, the system 708 of the present invention preserves the maximum amount of air in event of electrical power outage conditions. Also, locating the accumulator close to connector 150 and downstream of the air pressure regulating valves 792 and 794 helps ensure that the accumulator will best be able to dampen out pulsations or pressure variations inherently created in a low-pressure pneumatic pressure control system using on-off valves for charging and exhaust functions.

In the preferred embodiment of the present invention, the processor 324 monitors the output pressure of the IOP system 708 via transducer 742 and interface circuitry 540 shown in FIG. 4E, and selects for IOP system the most appropriate mode needed to produce or maintain the IOP output pressure as close as possible to the desired pressure setting selected by the user on console 46. The user selects the desired IOP pressure via one of the pairs of up/down buttons 58 front display 48 when the menu for IOP system is displayed.

The IOP system 708 thus operates under the control of processor 324. The control exercised over IOP system 708 by processor 324 can be best understood by way of the following example. Assume that a desired IOP pressure of 80 mmHg has just been selected by the user of console 46, that the IOP pressure is presently 0 aa mmHg, and that IOP system 708 is currently in its exhaust mode. To reach the desired level as quickly as possible without overshoot, processor 324 initially places system 708 in its fast charge mode. Then as the IOP pressure on line 780 comes within a predetermined distance (in terms of mmHg) of the desired pressure (such as within 10 or 15 mmHg), processor 324 switches system 708 to its slow charge mode, which causes pressure to rise at roughly half the rate of the fast charge mode. Then, when the desired pressure is obtained (plus or minus a suitable dead band such as one mmHg), processor 324 switches system 708 to its hold mode. Tests show that the system 708 does not exhibit any significant overshoot. However, if it did, the processor 324 would enter the exhaust mode to reduce the pressure slowly. As the actual pressure on line 780 reached the desired level, the processor 324 once again would switch to the hold state.

Whenever IOP system 708 is enabled, processor 324 obtains pressure readings obtained from transducer 384 at predetermined intervals of time (such as every 50 milliseconds), and as necessary processor 324 makes appropriate changes of mode then. In this manner, the IOP system 708 exhibits excellent response with very little if any overshoot. Further, tests show the use of accumulator 802 downstream of shutoff valve 696 reduced 4 mmHg pulsations exhibited by at least one prior art pneumatic system that used on/off charge and exhaust valves, to almost 0 mmHg.

D. Vitrectomy Control Section 710

The vitrectomy control section 710 delivers controlled pressure pulses to connector 146 on panel 90 of console 46. Conventional Storz MicroVit vitrectomy probes 140 include a guillotine-type cutter and are connected by an 80-inch-long medical-grade polyethylene tube 810 having an internal diameter of one-sixteenth inch to connector 146. The Storz DAISY console included an identical section 710, except that the separate 60 psi regulator 760 was not provided there. In both the DAISY console and console 46 shown in FIG. 1A, the cutting rate is selected by the user either (by a potentiometer) or buttons 58 when the vitrectomy procedure menu is displayed. The two-position, three-way solenoid-actuated, spring-returned control valve 812 is cyclically energized and de-energized at a rate equal to the desired vitrectomy cutting speed, provided that the user has pushed the appropriate button on footpedal assembly 240 (shown in FIG. 3) to initiate this cutting action. The regulator 760 has a maximum setting of 60 psig in order to avoid creating too much residual pressure at the higher cutting rates. At cutting rates above 690 cpm, tests show that the off time between pulses is so short relative to the amount of air resident in lines 810 and 814 that the air pressure does not have an opportunity to completely bleed off to atmosphere through valve 812 when de-energized. Thus pressure can build up. By having a separate regulator set to no more than 60 psig, the pressure can be kept from building up to undesirable levels (pressure greater than 3 psig). Also, it is desirable to keep the time that valve 812 is closed short enough so that the pressure never rises above 40 to 45 psig, and preferably only rises to about 31 psig, which is all the pressure that is required to completely close a Storz MicroVit probe under normal operating conditions.

E. Valve Manifold Control Section 712 The valve manifold section 712 includes six two-position, three-way, solenoid-actuated, spring-returned, valves, namely valves 818–828. Valves 818–822 and 826 drive spring-returned cylinders 717–720 as shown in FIG. 5. The cylinders 717 through 720 are respectively used for the following functions: cassette capture (which is actuated when the "cassette present" switch 602 indicates a cassette 72 has been fully inserted into slot 70); irrigation pinch assembly 76; aspiration pinch-off (squeezes section of pliable aspiration tubing running along top side of cassette 72); and reflux (squeezes aspirant tubing section adjacent to aspiration pinch-off tubing section to create the reflux action after the aspiration pinch-off is already actuated).

Valve 824 drives pilot line 830 leading to the pilot operator 832 of two-position, four-way, spring returned directional valve 722. Directional valve 722 directs pressurized proportional air flow from the servo valve 578 either to the venturi 730 (in order to produce a desired vacuum/aspiration level in tubing 736) or to line 836 and metered orifice 838 (which the bleeds line 840 to atmosphere). Note that when the solenoid of valve 824 is energized, valve 722 diverts a pressurized air from servo valve 578 to line 840, which delivers it to scissors connector 156 as well as orifice 156. The five solenoids 818–826 and cylinders 718–724, the servo valve 578 and the directional valve 722 as shown are all used in the Storz DAISY console. Air-to-vacuum converter 730 and its muffler 731 and transducer 744 are also employed in the Storz DAISY console.

In manifold section 712 the new features are the use of another control valve 828 (identical to valve 824) which pressurizes pilot line 848 connected to the pilot operator 850 of two-position three-way, spring return directional valve 723, that makes it possible to provide the three different scissors modes, including the high-speed multi-cut mode, through a single connector port 150, as will now be further explained below.

F. Microscissors Control Section

In the DAISY console, line 840 was connected directly to connector 156 for driving conventional microscissors in either a proportional cut mode or a single cut mode. In the single cut mode, the depression of the foot pedal more than a predetermined amount (e.g., 5 degrees while in the microscissors mode caused the servo valve 724 to turn on completely once for a brief period of time (several tens of milliseconds) which caused the spring-biased scissors to close and then open when the pressure subsided as a result of valve 224 returning to its closed position. In the proportional cut mode, the air pressure provided at connector board 156 varied in accordance with the amount which a user depressed the foot pedal on the footswitch assembly. As pressure at connector 156 rose, the bias of the mechanical spring in the microscissors was proportionately overcome, thereby causing the scissors to close by an amount proportionate to the applied air pressure. The applied air pressure is determined by use of the well-known air-pressure dividing circuit formed by a variable size orifice (i.e., the variable size orifice in servo valve 724) and a fixed size orifice (i.e., orifice 838). The larger the size of variable orifice in valve 724, the greater the air flow through valve 724 and the greater the pressure back pressure created at fixed orifice 838. As size of the variable orifice in valve 724 is reduced, there is less air flow and less back pressure created at orifice 838, and accordingly the pressure in line 840 drops. In this manner, the air pressure at scissors connector 156 was regulated. Transducer 743 was used to monitor the air pressure on line 40 and, using conventional feedback control techniques, the current being used to drive torque motor 725 of valve 724 was adjusted as necessary to reduce any feedback error (i.e. the difference between the desired pressure and actual pressure) to zero. All of this was accomplished using the microprocessor based control system in the Storz DAISY console. The pneumatic control system 43 of the present invention employs the same techniques for operating its single cut mode and proportional mode for the microscissors. When either of these two modes is desired, the solenoid of control valve 828 is left de-energized, so that there is a fluid passageway between line 840 and connector port 156 through valve 723. However, when a higher cut rate was requested, we determined that the servo valve 724, especially in combination with the air pressure dividing circuit just described, could not provide a high-speed pulsating signal (between 50 and 200 cycles per minute (cpm)) desired by some ophthalmic surgeons for microscissors operation. The Storz DAISY console is only capable of cutting at approximately 35 to 40 cpm maximum. In order to provide the desired high speed multi-cut mode, the present invention added control valves 723, 726 and 828. Control valve 726 when energized allows pressurized air from line 768 to flow through to line 850 connected to directional valve 723. When valve 726 is de-energized, line 850 is dumped to atmosphere. To achieve the multicut mode with the pneumatic system of the present invention, the solenoid of valve 828 is energized, which places pilot air on line 848, causing valve 723 to shift to its actuated position so that line 850 is tied to connector port 156. Thereafter, processor 324 causes control valve 726 to cycle at the desired rate selected by the user via console 46. FIG. 4E shows the control circuitry used to drive these solenoids, which have been previously explained.

G. Low-Pressure Monitoring System

As shown in FIG. 5, transducer 741 connected to line 764 monitors the main supply pressure from line 732 in order to determine whether it is adequate for all intended purposes to which the pneumatic system 43 may be put. In the Storz DAISY console, the pressure sensing means instead of transducer 741. pressure switch. Under selected conditions explained above in the background portion of this specification, the pressure in line 764 in the DAISY console could momentarily drop below the pressure switch setting, causing an indication through the pressure switch of low supply air pressure. In the DAISY console, this produced a warning to the surgeon of low air pressure. This, of course, is a very useful warning, since a surgeon may wish to instruct his operating room staff to take corrective action if the air supply appears to be low, which may happen on account of a clogged supply line or filter, low pressure in the supply tank or the like. Nevertheless, it was also determined that even with adequate air pressure supplied, there could exist, upon initiation of high air-flow rates used to create high levels of vacuums, a transient low-air pressure condition which also triggered this warning in the DAISY console. Further studies showed that as long as this transient condition does not last more than a predetermined length of time, such as 50 to 200 milliseconds, that there is no need to notify the surgeon of this problem. The cause for the momentary drop of pressure in line 764 when rapid air flow is initiated apparently is due to the inertia of the air in the lines when at rest. Of course, once the air flow is established, the air in the lines is moving, thus overcoming the inertia conditions, and this low air pressure condition goes away very rapidly, provided the air supply on line 700 is adequate. Studies also showed that the transient drop in air pressure under such conditions was small, typically down only 10 to 12 psi, so that the actual air pressure was in the neighborhood of 65 psi, which was lower than the pressure switch setting e.g., about 70–74 psi.

Further studies showed conventional pressure switches did not respond quickly enough and cannot be set accurately enough to measure such transient pressures reliably.

Accordingly, in the present invention, we replaced the pressure switch with a pressure transducer, which has much greater accuracy and far less hystersis. Further, the output of transducer 741 is an analog signal whose magnitude corresponds to the actual dynamic pressure within about one psi or less. Accordingly, use of transducer 741 allows processor 324 to take accurate readings of the pressure on line 764 to determine whether or not it has fallen below the acceptable minimum level of transient pressure in the range of 60–64 psi. Further, with its precision time base, processor 324 is also able to monitor with accuracy the length of time for which pressure transducer 741 is low.

Accordingly, when processor 324 sees the pressure reading from transducer 741 dip below the minimal continuously acceptable level (e.g., 72 psig), it watches to determine whether the actual pressure reading drops below a predetermined "critical" level (e.g. 60 psig). If it does, a low pressure warning is generated since such pressures are normally not encountered even upon initiation of high-levels of aspiration/vacuum. If however, the transient reduced pressure indicated by transducer 741 is not below this critical level, but is below the continuous acceptable level, the processor 324 monitors the length of time that the reading stays below the acceptable level (72 psi). If this continues more than a predetermined length of time, such as 200 milliseconds, then a low pressure warning is generated. If the transient low-pressure condition lasts less than this period of time, and a high-vacuum level has been called for by the user of console 46, processor 324 does not generate the low pressure warning. Thus this aspect of the present invention avoids nuisance occurrences of a safety procedure (e.g., the warning to the surgeon) during non-hazardous transient pressure situations, while still providing the capability of warning the surgeon when possibly serious low-pressure conditions exist in pneumatic control system 43.

VI. Technical Details of Pneumatics Drawer 44 (FIGS. 6 & 7)

A. Overview

Figure 6:
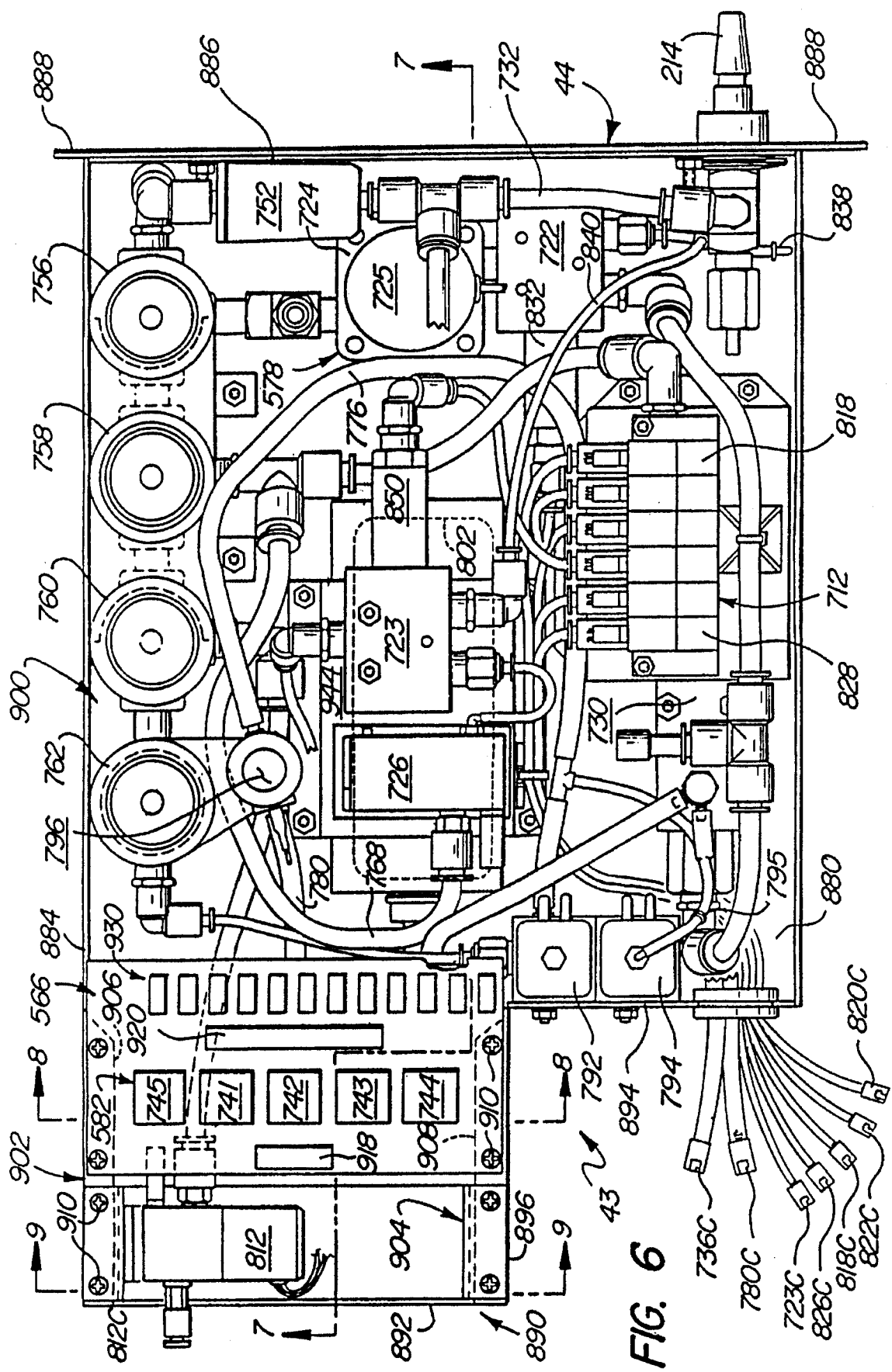
FIG. 6 is a plan view of a pneumatics drawer assembly of the present invention showing the preferred location of various components within the FIG. 5 pneumatic system.
Figure 7:
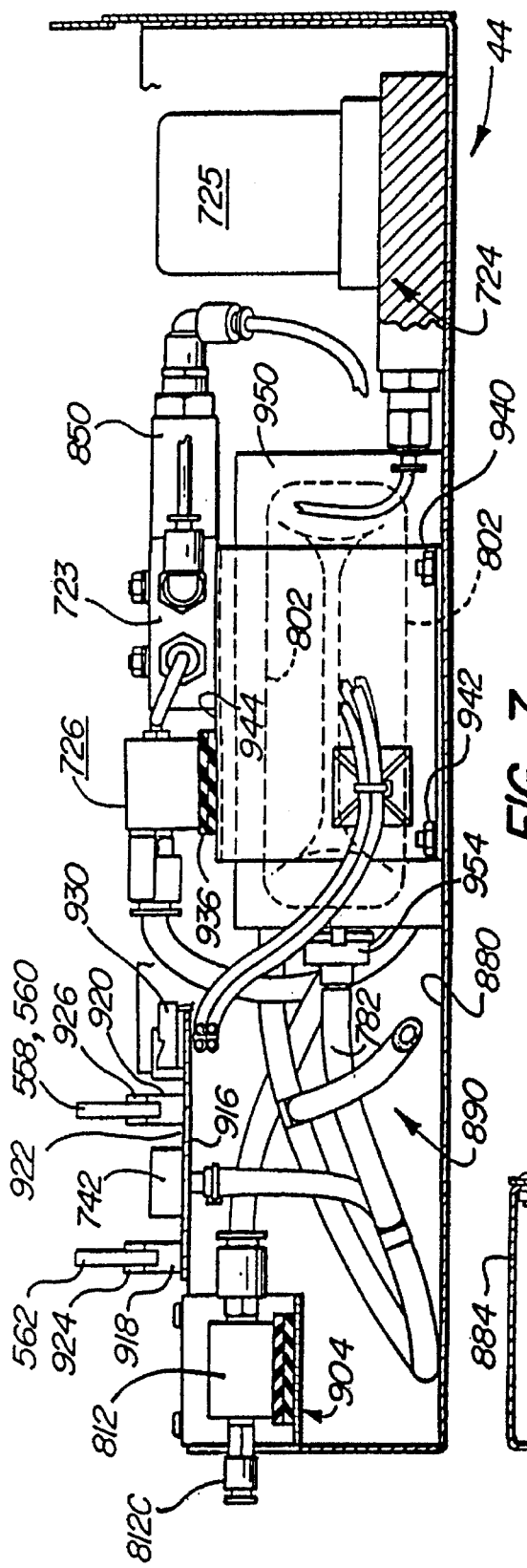
FIG. 7 is a longitudinal cross-sectional view of the FIG. 6 pneumatics drawer taken along line 7—7 in FIG. 5.

FIGS. 6 and 7 show plan and side cross-sectional views of the pneumatics drawer assembly 44 which holds most of the pneumatic system 43. Drawer 44 includes: a flat bottom 880 and side walls 882 and 884; a front drawer or face wall 886 provided with a painted cover plate 888 fastened thereto and extending somewhat beyond the side walls; and a rear wall structure 890 having two back wall portions 892 and 894, and an intermediate side wall portion 896 extending between back wall portions 892 and 894. The main drawer chamber section 900 is filled with various pneumatic components, conventional tubing and electrical wires (not shown) for the solenoids, while the secondary drawer portion 902 in the rear of drawer 44 contains only the vitrectomy solenoid valve 812 on its own support shelf 904, the connector board assembly 566 and a limited amount of pneumatic tubing. Side walls 884 and 896 are provided with flanges 906 and 908 which support the shelf 904 and printed circuit (PC) board assembly 566, which are both held on by screws 910 or other suitable fastening means. The structural part of drawer 44 may be made from any suitable material such as sheet metal, molded plastic, or the like.

B. PC Board 556 and Support Shelf 904 (FIGS. 7, 8 and 9)

Figure 8:
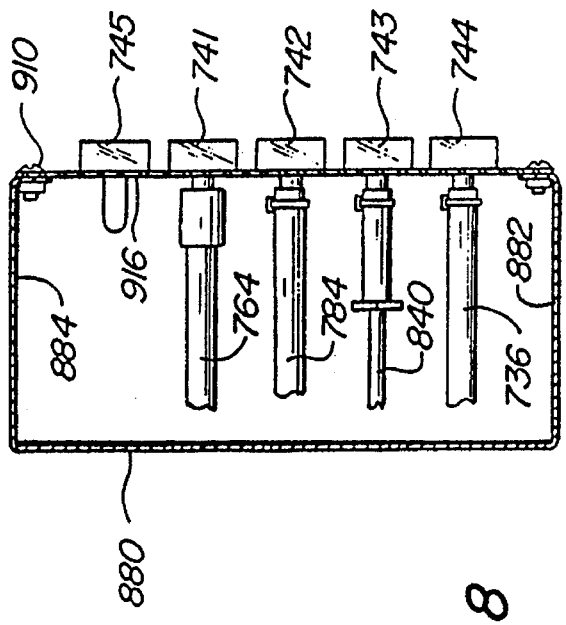
FIG. 8 is a cross-sectional view taken along line 8—8 of FIG. 5 showing an electrical connector board.
Figure 9:
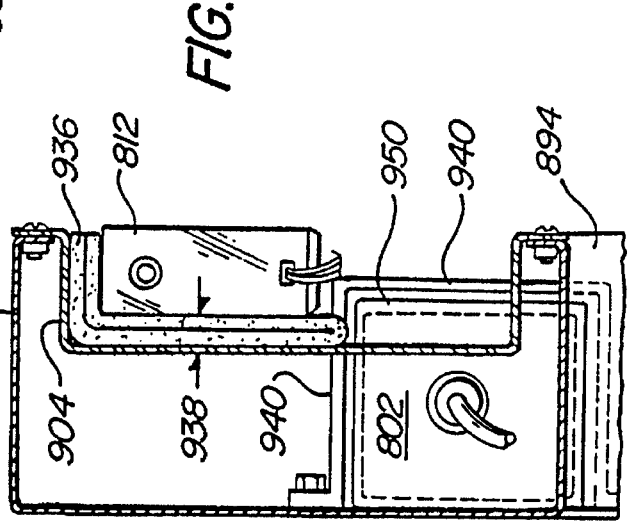
FIG. 9 is a cross-sectional view taken along line 9—9 of FIG. 5 and showing the shelf and vibration dampening material supporting an electrically operated solenoid valve.

FIGS. 7, 8 and 9 are cross-sectional views taken along lines 7—7, 8—8 and 9—9 of FIG. 6, which better illustrate the details of the construction of PC board assembly 556 and support shelf 904. As previously explained with respect to FIG. 4E, the connector board 566 does not contain any electronic circuitry, but instead is simply used as a convenient termination point for the internal electrical wires 568–570 and 572 connected to the torque motor valve 578, the solenoids 580 and pressure transducers 582 used in the pneumatics drawer 44. Connector board assembly 566 includes a conventional PC circuit board 916 having metallic conductor traces as needed, two conventional electrical multiple-pin, straight-line connector receptacles 918 and 920 mounted on the upper face 922 of the PC board which receive mating connector plugs 924 and 926, the set 582 of pressure transducers 741–745 arranged in a line, and a set 930 of conventional single-screw pressure terminal-to-PC-board connectors used to receive the individual conductors 578 and 570 from solenoid valve 578 and the set 580 of solenoids (see FIG. 4E). The transducer conductors 572 are wired directly on the PC board to the receptacle 918. The individual terminals 930 are wired directly on the PC board to connector receptacle 920. Thus, as may be best understood by referring to FIG. 4E and FIG. 7, all of the transducer conductors 552 running between pneumatics drawer hardware 360 and the pneumatics control PC board 350 run through connector 918, while all the torque motor conductors 558 and solenoid conductors 560 run through connector 920.

One important benefit of PC connector board 566, then, is that it can be pre-assembled with all its components on it well ahead of the actual need for the board. Thus PC board assemblies 556 can be stockpiled as needed for manufacturing purposes. Once board 556 is attached to flanges 906 and 908 in drawer 44, it is an easy matter to hook color-coded electrical wires (not shown) from the solenoid valves to terminals 930, and to plug in connector plugs 924 and 926 to complete the electrical connections to the pneumatics drawer assembly. Just prior to the board 556 being fastened to the flanges, the pneumatic lines 736, 764, 784 and 840 are attached to the transducers, as shown in FIG. 8. Plenty of room is provided in rear drawer section 890 of drawer 44 for the tubing to snake around as necessary to avoid kinking, as may be best seen on the left side of FIG. 7, when the board 566 is pressed down and fastened to flanges 906 and 908.

Referring now to FIGS. 6–7 and 9, the support shelf 904 for vitrectomy solenoid valve 812 is shown. The shelf has a U-shaped cross section, as best seen in FIG. 9, and the valve 812 is mounted on vibration-dampening material 936 which is preferably blow-molded foam material with adhesive on all sides thereof. In the preferred embodiment, the material 936 is made from one eighth inch mounting tape doubled over for double thickness (i.e., dimension 938 is one-quarter inch). Material 936 may be double-sided adhesive-backed mounting tape available from Minnesota, Mining and Manufacturing Company of Minneapolis, Minn. under adhesive tape Pad No. 4408. As may best be seen in FIG. 7, the high-speed control valve 726 for the multi-cut scissors operation is also mounted using this same material 936 on top of a sheet metal support bracket 940 having a U-shaped cross section as best seen in FIG. 9.

C. Support Bracket 940 & Component Arrangement (FIGS. 6–9)

The U-shaped bracket 940 shown best in FIGS. 7 and 9 is fastened by screws and nuts 942 or the like to drawer bottom 880. Also mounted on the upper surface 944 of support bracket 940 is the pilot-operated, two-position, three-way spring returned directional valve 723, with its pilot operator 850 overhanging the side of stanchion 940. Positioned underneath support bracket 940 is a transparent plastic protective rectangular housing 950 for the silicone rubber bladder which serves as accumulator 802 shown in phantom within housing 950. Line 782 is connected to a conventional pneumatic fitting assembly 954 attached to housing 950 and to bladder 802 within the housing. The bladder is typically made of very pliant material such as natural rubber because it must be able to expand at very low pressures reliably and repeatably without tearing. Protective housing 850 makes sure the bladder is not inadvertently scratched or punctured by other objects during the assembly of or use of pneumatics drawer 44.

The arrangement of various pneumatic components within the large chamber 900 of drawer 44 is designed to maximize efficient use of space, which allows the drawer 44 to be made smaller. Yet the large section 900 of drawer 44 is not so crowded that it is difficult to make the various connections shown. In assembly, a number of the devices, fittings, and tubing sections can be connected together before they are mounted or fastened into the enclosure 44 by screws, adhesives or other suitable fastening means. The pressurized air supply comes in on hospital grade Schrader fitting 214 and runs through main filter 752 near the face plate 888 the drawer and then to the four regulators 756–762 arranged in a row. The use of valve manifold assembly 712 including valves 818–828 reduces the space requirements so that virtually all of the other control components can readily fit within the small volume of section 900. In the preferred embodiment, the size of the drawer is approximately 13.5 inches deep (i.e., the distance between the two parallel front and back wall portions 886 and 892), and 8.4 inches wide (i.e., the distance between the upstanding parallel side walls 882 and 884). The total height of the drawer is less than 4.0 inches. The drawer thus can easily fit within the larger cabinet of control console 46, without taking up much room.

FIG. 6 shows all of the eight pneumatic lines which exit the drawer 44. These connections am all conventional quick-disconnect pneumatic fittings for 1/16 inch ID or 1/8 inch ID tubing. In the preferred embodiment, fitting Model Nos. SMC-01 and No. SMC-02 from Colder Products, of St. Paul, Minn. are used.

On FIG. 5, each of the pneumatic lines on which quick-disconnect fittings are used has been marked with an "X". All of the eight output lines from drawer 44 have quick-disconnect fittings on them are appropriately marked by reference numerals with the suffix "C" in FIG. 5. For example, the vitrectomy control section 710 includes solenoid valve 812 whose output line is tubing line 814. This line extends outside of drawer 44 to connector 146 on the connector panel 90 of console 46. This line 814 is broken by quick disconnect connector assembly as shown by the "X" identified by reference numeral 812C. In a similar manner, the line 780 of IOP section 708 includes quick-disconnect coupling 780C.

The use of these quick-disconnect couplings on all output lines permits the drawer assembly 44 to be readily installed or removed from the control console by simply connecting or disconnecting output pneumatic lines at these quick-disconnect points. As previously mentioned, the electrical connections are also only made through two electrical connectors 924 and 926, that are pushed into connector receptacles 918 and 920, so these are just as easily installed or removed. Thus the pneumatics module in drawer 44 is readily portable, compact, of rugged construction and easy to install or remove. Since the modular pneumatics assembly of drawer 44 can be entirely assembled prior to constructing the cabinet, this also saves much time in the final assembly of control console 46. This also makes it much easier to service, prepare and/or replace virtually the entire pneumatic control system of console 44, should that ever prove necessary.

D. Components for Pneumatic System 43

All of the control devices used within the presently preferred embodiment of pneumatics drawer assembly 44 are conventional pads purchased from commercial suppliers of such devices. The following is a Table listing a number of the more important devices by reference numeral used in the foregoing description, as well as the company from which such pads are available.

TABLE 2

| Ref. No(s). | Brief Name | Model No. or Part No./Source |
|---|---|---|
| 528 | servo valve | No. 100-521-1 Hydraulic Servo Controls, Inc. Buffalo, New York |
| 712 | valve manifold | No. NVJ100 SMC Pneumatics, Inc. Indianapolis, Indiana |
| 726, 812 | control valve, three-way | No. NZ 3125-0151BG (12 VDC) SMC Pneumatics, Inc. Indianapolis, Indiana |
| 730 | venturi | No. 33-S K & K Engineering, Inc. Wheeling, Illinois |
| 741–744 | pressure transducers | No. PC134 Series Microswitch, division of Honeywell Freeport, Illinois |
| 752 | air filter, submicron | No. 9900-05-BK Balston Filter Lexington, Massachusetts |
| 762 | regulator, low press. | No. R06-131-RNKA Norgren Corp. Littleton, Colorado |
| 792–794 | control valve, two-way | Mini-mizer No. M3E1 Humphrey, Inc. Kalamazoo, Michigan |
| 796 | control valve | No. Et-2 (12 VDC) Clippard Instrument Laboratory, Inc. Cincinnati, Ohio |
| 802 | accumulator | 3-inch Gordon Goodman Bladder Custom Service Labs of New Jersey Inc. North Bergen, New Jersey |
| 818–826 | control valve, three-way | No. NVJ114-6MZ SMC Pneumatics, Inc. Indianapolis, Indiana |

Any other conventional or suitable control devices may be used in place of the particular brands or part numbers of control equipment mentioned herein, since the present invention resides, not in the choice of any one particular component, but instead in the unique and cooperative combination and effect achieved by the various portions of the surgical instrument control system described herein, and in the methods of using same.

VII. Epilogue

The foregoing detailed description shows that the preferred embodiments of the present invention are well suited to fulfill the objects above-stated. It is recognized that those in the art may make various modifications or additions to the preferred embodiments chosen to illustrate the present invention without departing from the spirit and proper scope of the present invention. For example, different styles of control valves or pressure transducers may be utilized, and the pneumatic control system may be implemented using more manifold-mounted pneumatic circuit components. Accordingly, it is to be understood that the protection sought and to be afforded hereby should be deemed to extend to the subject matter defined by the appended claims, including all fair equivalents thereof.

We claim:

1. A pneumatic control system for ophthalmic microsurgical console constructed as a module for easy placement and connection into a larger cabinet for the console, comprising: at least three air pressure regulators; at least four solenoid control valves; a plurality of air pressure sensing devices; a drawer assembly having a generally planar bottom structure, first and second side wall structures arranged parallel to one another and extending upwardly from the bottom, and a third wall structure arranged generally perpendicularly to the side walls and extending upwardly from the bottom structure, the regulators, solenoid control valves and air pressure sensing devices all being located substantially within and mounted to the drawer assembly.

2. A control system as in claim 1, further comprising: a multi-pin electrical connector assembly; a plurality of quick-connect electrical terminals; bracket means mounted to the drawer structure for supporting the pressure sensing devices, the multi-pin electrical connector assembly and the plurality of electrical terminals; and a plurality of electrical conductors extending between the quick-connect electrical terminals and the multi-pin electrical connector assembly, and wherein the plurality of air pressure sensing devices includes at least two pressure transducers.

3. A control system as in claim 1, further comprising: low pressure accumulator means, forming pad of an intraocular pressure system, for temporary storage of low pressure air, the accumulator means including a flexible expandable bladder made at least in pad with soft pliant material; and housing means for protecting the bladder of the accumulator means from accidental damage, the housing means being rigidly attached to and located within the drawer structure.

4. A control system as in claim 3, wherein: the air pressure regulators are arranged in a line, the solenoid control valves are arranged in a line, and the control system further comprises: a main air supply connector mounted to and extending outside of the drawer assembly and arranged substantially in line with the line of air pressure regulators.

* * * * *